US011567060B2

(12) United States Patent
Boyanov et al.

(10) Patent No.: US 11,567,060 B2
(45) Date of Patent: Jan. 31, 2023

(54) NANOPORE SEQUENCERS

(71) Applicant: ILLUMINA, INC., San Diego, CA (US)

(72) Inventors: Boyan Boyanov, San Diego, CA (US); Rohan N. Akolkar, Beachwood, OH (US); Jeffrey S. Fisher, San Diego, CA (US); Jeffrey G. Mandell, La Jolla, CA (US); Liangliang Qiang, San Diego, CA (US); Steven M. Barnard, Delmar, CA (US)

(73) Assignee: Illumina, Inc., San Diego, CA (US)

( * ) Notice: Subject to any disclaimer, the term of this patent is extended or adjusted under 35 U.S.C. 154(b) by 451 days.

(21) Appl. No.: 16/624,567

(22) PCT Filed: Jun. 19, 2018

(86) PCT No.: PCT/US2018/038337
§ 371 (c)(1),
(2) Date: Dec. 19, 2019

(87) PCT Pub. No.: WO2018/236906
PCT Pub. Date: Dec. 27, 2018

(65) Prior Publication Data
US 2020/0132664 A1 Apr. 30, 2020

Related U.S. Application Data

(60) Provisional application No. 62/522,628, filed on Jun. 20, 2017.

(51) Int. Cl.
*G01N 33/487* (2006.01)
*C12Q 1/6869* (2018.01)
*G01N 27/447* (2006.01)

(52) U.S. Cl.
CPC ..... *G01N 33/48721* (2013.01); *C12Q 1/6869* (2013.01); *G01N 27/44791* (2013.01)

(58) Field of Classification Search
None
See application file for complete search history.

(56) References Cited

U.S. PATENT DOCUMENTS 7,163,658 B2 1/2007 Bension
9,429,561 B2 8/2016 Burrows et al.
(Continued)

FOREIGN PATENT DOCUMENTS

CA 2698876 A1 3/2009
CA 3001621 A1 5/2017
(Continued)

OTHER PUBLICATIONS

Bezrukov, S.M et al."Field-Dependent Effect of Crown Ether (18-Crown-6) on Ionic Conductance of a-Hemolysin Channels", Biophysical Journal, vol. 87, pp. 3162-3171, 2004.
Heins, E. A et al."Effect of Crown Ether on Ion Currents through Synthetic Membranes Containing a Single Conically Shaped Nanopore", Journal of Physical Chemistry, vol. 109, pP. 18400-18407, 2005.
Guo, W et al."Asymmetric Ion Transport through Ion-Channel-Mimetic Solid-State Nanopores", Accounts of Chemical Research, vol. 46, No. 12, pp. 2834-2846, 2013.
(Continued)

*Primary Examiner* — J. Christopher Ball
(74) *Attorney, Agent, or Firm* — Illumina, Inc.

(57) ABSTRACT

Example nanopore sequencers include a cis well, a trans well, and a nanopore fluidically connecting the cis and trans wells. In one example sequencer, a modified electrolyte (including an electrolyte and a cation complexing agent) is present in the cis well, or the trans well, or in the cis and the trans wells. In another example sequencer, a gel state
(Continued)

polyelectrolyte is present in the cis well, or the trans well, or in the cis and the trans wells.

21 Claims, 6 Drawing Sheets

(56) References Cited

U.S. PATENT DOCUMENTS

| | | | |
|---|---|---|---|
| 2010/0025238 | A1 | 2/2010 | Gottlieb et al. |
| 2010/0035260 | A1 | 2/2010 | Olasagasti et al. |
| 2010/0072080 | A1 | 3/2010 | Karhanek et al. |
| 2014/0021047 | A1 | 1/2014 | Shim et al. |
| 2014/0190833 | A1 | 7/2014 | Lieber et al. |
| 2015/0111759 | A1 | 4/2015 | Ju et al. |
| 2015/0185200 | A1 | 4/2015 | Burrows et al. |
| 2015/0219593 | A1 | 8/2015 | Kawai et al. |
| 2015/0265994 | A1 | 9/2015 | Hyde et al. |
| 2017/0058336 | A1 | 3/2017 | Ivankin et al. |
| 2017/0168040 | A1 | 6/2017 | Turner et al. |

FOREIGN PATENT DOCUMENTS

| | | |
|---|---|---|
| CN | 103842519 | 6/2014 |
| CN | 104583767 | 4/2015 |
| EA | 022475 | 1/2016 |
| JP | 2015521030 | 7/2015 |
| JP | 2016127851 | 7/2016 |
| RU | 2014149813 | 7/2016 |
| WO | WO 2011/130312 | 10/2011 |
| WO | 2012.138357 | 10/2012 |
| WO | WO 2016/196755 | 12/2016 |

OTHER PUBLICATIONS

Lin, X.H et al. "Poisson-Fokker-Planck model for biomolecules translocation through nanopore driven by electroosmotic flow", Science China, vol. 57, No. 11, pp. 2104-2113, 2014.

Hsiao, P. "Polyelectrolyte Threading Through a Nanopore", Polymers, 2016, vol. 8, Article No. 73, pp. 1-20.

International Search Report and Written Opinion for International Application No. PCT/US2018/038337 dated Jan. 21, 2019, 14 pages.

An, N. et al. "Crown Ether-Electrolyte Interactions Permit Nanopore Detection of Individual DNA Abasic Sites in Single Molecules", PNAS, Jul. 17, 2012, vol. 109, No. 29, p. 11504-11509.

Geiss, F. et al. "The Protein-Tethered Lipid Bilayer: A Novel Mimic of the Biological Membrane", Biophysical Journal, vol. 87, Nov. 2004, pp. 3213-3220.

Bard, S., "Investigation of Ion-Peptide Interactions Using a Biocompatible Nanopore Probe", A Thesis Submitted to the Office of Graduate Studies of Texas A&M University, May 2012.

Cornelius, G., et al., "Cation Complexation by Valinomycin- and Nigericin-Type Ionophores Registered by the Fluorescence Signal of Tl+ ion", Biochemistry. 1974, vol. 13, No. 15, pp. 3052-3057, 1974.

Arnaud-Neu, F., et al., "Cation Complexation by Chemically Modified Calixarenes. Part 7. Transport of Alkali Cations by p-tert-Butylcalix[n]arene Esters and Amides", Chem. Soc., Perkin Trans. 2., pp. 113-118, 1995.

US 11,567,060 B2

NANOPORE SEQUENCERS

CROSS-REFERENCE TO RELATED APPLICATIONS

This application is a national stage entry under 35 U.S.C. § 371 of PCT/US2018/038337, filed Jun. 19, 2018, which itself claims the benefit of U.S. Provisional Application Ser. No. 62/522,628, filed Jun. 20, 2017, the content of each of which is incorporated by reference herein in its entirety.

BACKGROUND

Various polynucleotide sequencing techniques involve performing a large number of controlled reactions on local support surfaces or within predefined reaction chambers. The designated reactions may then be observed or detected, and subsequent analysis may help identify or reveal properties of the polynucleotide involved in the reaction. Another polynucleotide sequencing technique has been developed that utilizes a nanopore, which can provide a channel for an ionic electrical current. A polynucleotide is driven through the nanopore, and as the polynucleotide passes through the nanopore, it disrupts the electrical current through the nanopore. Each passing nucleotide, or series of nucleotides, yields a characteristic electrical current, and the record of the current levels corresponds to the sequence of the polynucleotide.

SUMMARY

An example of the nanopore sequencer disclosed herein includes a cis well; a trans well; a nanopore fluidically connecting the cis well and the trans well; and a modified electrolyte in the cis well, or the trans well, or the cis and trans wells, the modified electrolyte including an electrolyte and a cation complexing agent.

Another example of the nanopore sequencer disclosed herein includes a cis well; a trans well; a nanopore fluidically connecting the cis well and the trans well; and a polyelectrolyte in a gel state in the cis well, or the trans well, or the cis and trans wells.

Still another example of a nanopore sequencer includes a cis well; a trans well; a nanopore fluidically connecting the cis well and the trans well; a cis well electrode structure associated with the cis well, the cis well electrode structure including a first base electrode and a redox solid immobilized to the first base electrode; a trans well electrode structure associated with the trans well, the trans well electrode structure including a second base electrode and the redox solid immobilized to the second base electrode; and an electrolyte including a cation to be consumed or released in response to respective redox reactions at the first electrode structure and the second electrode structure.

BRIEF DESCRIPTION OF THE DRAWINGS

Features of examples of the present disclosure will become apparent by reference to the following detailed description and drawings, in which like reference numerals correspond to similar, though perhaps not identical, components. For the sake of brevity, reference numerals or features having a previously described function may or may not be described in connection with other drawings in which they appear.

INTRODUCTION

Figure 1:
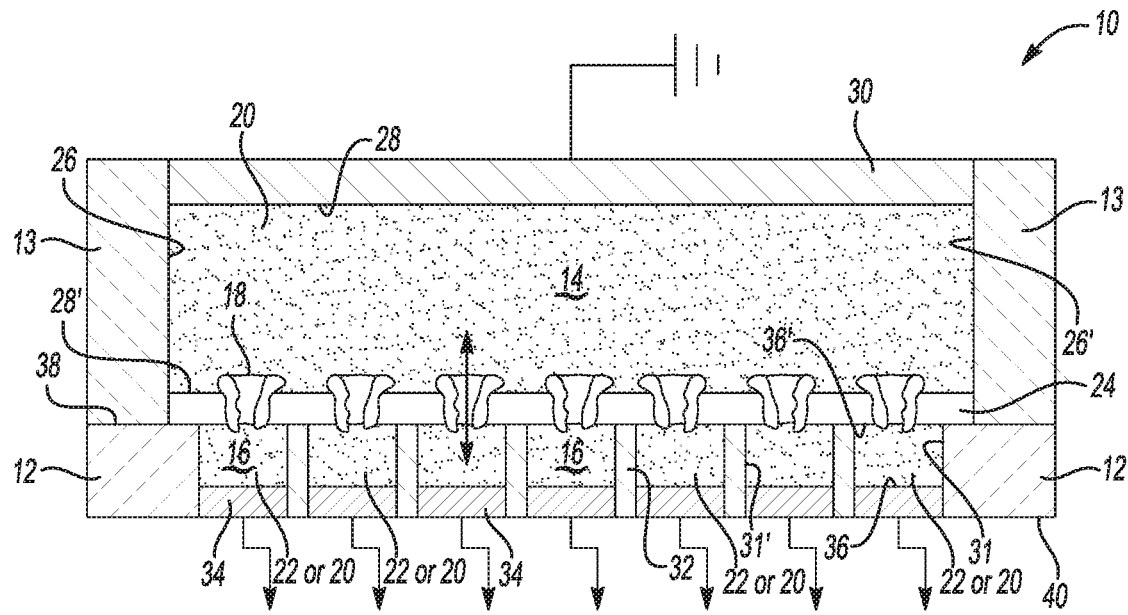
FIG. 1 is a schematic and partially cross-sectional view of an example of a nanopore sequencer disclosed herein.

In a first aspect, a nanopore sequencer, comprises a cis well; a trans well; a nanopore fluidically connecting the cis well and the trans well; and a modified electrolyte in the cis well, or the trans well, or the cis and trans wells, the modified electrolyte including an electrolyte and a cation complexing agent.

In one example of this first aspect, the modified electrolyte is in the cis well, the nanopore sequencer further comprises a non-modified electrolyte in the trans well, and the non-modified electrolyte includes the electrolyte without the cation complexing agent; or the modified electrolyte is in the trans well, the nanopore sequencer further comprises the non-modified electrolyte in the cis well, and the non-modified electrolyte includes the electrolyte without the cation complexing agent.

In another example of this first aspect, the nanopore sequencer further comprises a plurality of the trans wells defined in a substrate, each of which is fluidically connected to the cis well by a respective nanopore, wherein a density of the plurality of trans wells ranges from about 10 trans wells per mm$^2$ of the substrate to about 1,000,000 trans wells per mm$^2$ of the substrate.

In still another example of this first aspect, the electrolyte includes a potassium cation and an associated anion, a sodium cation and an associated anion, or combinations thereof; and the cation complexing agent is selected from the group consisting of a crown ether, a calixarene, and valinomycin.

In yet another example of this first aspect, the modified electrolyte includes greater than 0 mM to about 500 mM of the cation complexing agent.

It is to be understood that any features of this first aspect of the nanopore sequencer may be combined together in any desirable manner and/or configuration.

In a second aspect, a nanopore sequencer comprises a cis well; a trans well; a nanopore fluidically connecting the cis well and the trans well; and a polyelectrolyte in a gel state in the cis well, or the trans well, or the cis and trans wells.

In one example of this second aspect, the polyelectrolyte is in the cis well and the nanopore sequencer further comprises an electrolyte in the trans well; or the polyelectrolyte is in the trans well and the nanopore sequencer further comprises an electrolyte in the cis well. In an example, the polyelectrolyte is selected from the group consisting of polydiallyldimethylammonium chloride, an ionic form of polyethyleneimine, an ionic form of linear polyethyleneimine, poly(allylamine hydrochloride), and an ionic form of poly(4-vinylpyridine); and the electrolyte includes a potassium cation and an associated anion, a sodium cation and the associated anion, or combinations thereof.

In another example of this second aspect, the nanopore sequencer further comprises a plurality of the trans wells defined in a substrate, each of which is fluidically connected to the cis well by a respective nanopore, and wherein a density of the plurality of trans wells ranges from about 10 trans wells per $mm^2$ of the substrate to about 1,000,000 trans wells per $mm^2$ of the substrate.

In still another example of this second aspect, the polyelectrolyte is present in both the cis and trans wells; and the polyelectrolyte is selected from the group consisting of polydiallyldimethylammonium chloride, an ionic form of polyethyleneimine, an ionic form of linear polyethyleneimine, poly(allylamine hydrochloride), and an ionic form of poly(4-vinylpyridine).

It is to be understood that any features of the second aspect of the nanopore sequencer may be combined together in any desirable manner. Moreover, it is to be understood that any combination of features of the first aspect of the nanopore sequencer and/or of the second aspect of the nanopore sequencer may be used together, and/or that any features from either or both of these aspects may be combined with any of the examples disclosed herein.

In a third aspect, a nanopore sequencer comprises a cis well; a trans well; a nanopore fluidically connecting the cis well and the trans well; a cis well electrode structure associated with the cis well, the cis well electrode structure including a first base electrode and a redox solid immobilized to the first base electrode; a trans well electrode structure associated with the trans well, the trans well electrode structure including a second base electrode and the redox solid immobilized to the second base electrode; and an electrolyte including a cation to be consumed or released in response to respective redox reactions at the cis well electrode structure and the trans well electrode structure.

In an example of this third aspect, the redox solid is selected from the group consisting of tetracyanoquinodimethane (TCNQ), Prussian blue, and polypyrrole.

In another example of this third aspect, the first and second base electrodes are independently selected from the group consisting of graphite, platinum, gold, silver, copper, carbon fiber, diamond, and palladium.

It is to be understood that any features of the third aspect of the nanopore sequencer may be combined together in any desirable manner. Moreover, it is to be understood that any combination of features of the third aspect of the nanopore sequencer and/or of the second aspect of the nanopore sequencer and/or of the first aspect of the nanopore sequencer may be used together, and/or that any features from any one or more of these aspects may be combined with any of the examples disclosed herein.

In a fourth aspect, a method of using the nanopore sequencer according to the first aspect comprises controlling depletion of a redox reagent of the electrolyte in the nanopore sequencer by applying a voltage bias ranging from about −1 V to about 1 V between the cis well of the nanopore sequencer and the trans well of the nanopore sequencer.

In an example of this fourth aspect, the method further comprises providing the nanopore sequencer with: the modified electrolyte in the cis well, and the electrolyte, without the cation complexing agent, in the trans well; or the modified electrolyte in the trans well, and the electrolyte, without the cation complexing agent, in the cis well.

In another example of this fourth aspect, the method further comprises incorporating the cation complexing agent into the electrolyte to form the modified electrolyte; and introducing the modified electrolyte to the cis well, or the trans well, or the cis and trans wells.

In still another example of this fourth aspect, the electrolyte includes a potassium cation and an associated anion, a sodium cation and the associated anion, or combinations thereof; and the cation complexing agent is selected from the group consisting of a crown ether, a calixarene, and valinomycin.

It is to be understood that any features of the fourth aspect of the method may be combined together in any desirable manner. Moreover, it is to be understood that any combination of features of the fourth aspect of the method and/or of the third aspect of the nanopore sequencer and/or of the second aspect of the nanopore sequencer and/or of the first aspect of the nanopore sequencer may be used together, and/or that any features from any one or more of these aspects may be combined with any of the examples disclosed herein.

In a fifth aspect, a method of using the nanopore sequencer according to the second aspect comprises controlling depletion of a redox reagent of the polyelectrolyte in the nanopore sequencer by applying a voltage bias ranging from about −1 V to about 1 V between the cis well of the nanopore sequencer and the trans well of the nanopore sequencer.

It is to be understood that any features of the fifth aspect of the method may be combined together in any desirable manner. Moreover, it is to be understood that any combination of features of the fifth aspect of the method and/or of the fourth aspect of the method and/or of the third aspect of the nanopore sequencer and/or of the second aspect of the nanopore sequencer and/or of the first aspect of the nanopore sequencer may be used together, and/or that any features from any one or more of these aspects may be combined with any of the examples disclosed herein.

In a sixth aspect, a method of using the nanopore sequencer according to the third aspect comprises controlling depletion of a redox reagent of the electrolyte in the nanopore sequencer by applying a first voltage to the cis well electrode structure, thereby initiating a cathodic reaction that consumes a cation of the electrolyte in the nanopore sequencer; and applying a second voltage to the trans well electrode structure, thereby initiating an anodic reaction that releases the cation of the electrolyte.

In an example of the sixth aspect, the redox solid is selected from the group consisting of tetracyanoquinodimethane (TCNQ), Prussian blue, and polypyrrole.

It is to be understood that any features of the sixth aspect of the method may be combined together in any desirable manner. Moreover, it is to be understood that any combination of features of the sixth aspect of the method and/or of the fifth aspect of the method and/or of the fourth aspect of the method and/or of the third aspect of the nanopore sequencer and/or of the second aspect of the nanopore sequencer and/or of the first aspect of the nanopore sequencer may be used together, and/or that any features from any one or more of these aspects may be combined with any of the examples disclosed herein.

DETAILED DESCRIPTION

The technique of nanopore sequencing uses variations in current to distinguish nucleotide bases. In nanopore sequencers, one electrolyte redox reagent may be partially consumed on a trans well (or chamber) electrode in order to support Faradaic current through the system. The partially consumed electrolyte redox reagent may not be efficiently replenished on a corresponding cis well electrode, due, in part, to ion transport inhibition through the nanopore(s). For example, chloride anions may be partially depleted on the trans side due to plating and may not be fully replenished on the cis side. A concentration gradient develops for both of the electrolyte redox reagents (e.g., cation and anion), and a new equilibrium is established at a much lower concentration of the partially depleted reagent on the trans side. The imbalance of electrolyte redox reagent transport through the nanopore versus the partial consumption of one of the reagents on the trans electrode can cause current drift, which can deleteriously affect the ability to distinguish between nucleotide bases.

The partial consumption of the electrolyte redox reagent depends on several factors, including the starting concentration of the electrolyte redox reagent, the current that passes through the nanopore, and the size of the trans chamber (e.g., larger chambers are generally associated with less reagent consumption and smaller chambers are generally associated with more reagent consumption).

Partial consumption may be evidenced by a reduction in the initial reagent concentration, where the reduction is greater than a factor of 10. In some instances, the reduction ranges from a factor of 20 to a factor of 100. For example, the chloride concentration of an electrolyte having an initial chloride concentration of about 300 mM in a 10 μm trans well can be depleted to about 10 mM, and thus the initial concentration is reduced by a factor of about 30. For another example, the chloride concentration of an electrolyte having an initial chloride concentration of about 10 mM in a 10 μm trans well can be depleted to about 0.1 mM, and thus the initial concentration is reduced by a factor of about 100. It is to be understood that the partial consumption/depletion can approach 100% (i.e., the electrolyte redox reagent remaining in the system approaches 0%), but an equilibrium will establish between the electrolyte redox reagents, even at such low levels of the partially consumed reagent.

Examples of the nanopore sequencer and method disclosed herein effectively reduce the partial consumption or depletion of the electrolyte redox reagent(s) at the trans well (or chamber) electrode(s) of the sequencer. In the examples disclosed herein, a reduction in the initial reagent concentration may still occur; however, the reduction is less than 10% and likely less than 1%. As such, more of the reagent is present over time (e.g., compared to the examples provided above), and thus consumption or depletion of the reagent is reduced. Some examples reduce partial electrolyte redox reagent consumption/depletion by mitigating the diffusion of an electrochemically passive species (e.g., electrolyte cations) through nanopore(s) of the sequencer. In some examples, the electrochemically passive species is an electrolyte cation. Mitigating the diffusion of the cations enables the charge to be carried exclusively by the anions of the electrolyte. By exclusively using the anions as the charge carriers (as opposed to charge being carried by both the anions and the cations), any charge imbalance between the anion supply and the anion consumption is at least reduced. As a result, anion depletion from trans well(s) of the nanopore sequencer is also reduced. Other examples at least reduce electrolyte anion consumption/depletion by incorporating an electrode system that does not consume the anions, but rather generates the electrolyte cations at one electrode and consumes the same electrolyte cations at the other electrode.

As mentioned above, the technique of nanopore sequencing uses variations in current to distinguish nucleotide bases. A depletion in the electrolyte species results in a depletion (or undesirable shift) in current, which deleteriously affects the ability to obtain accurate current readings for the nucleotide bases. By balancing the ionic species transport through the nanopore with the consumption of that species at the trans electrode, current drift may be mitigated and the lifetime of the electrolyte, the trans electrode, and the trans well may be increased.

It is to be understood that terms used herein will take on their ordinary meaning in the relevant art unless specified otherwise. Several terms used herein and their meanings are set forth below.

The singular forms "a", "an", and "the" include plural referents unless the context clearly dictates otherwise.

The terms comprising, including, containing and various forms of these terms are synonymous with each other and are meant to be equally broad. Moreover, unless explicitly stated to the contrary, examples comprising, including, or having an element or a plurality of elements having a particular property may include additional elements, whether or not the additional elements have that property.

As used herein, the terms "fluidically connecting," "fluid communication," "fluidically coupled," and the like refer to two spatial regions being connected together such that a liquid or gas may flow between the two spatial regions. For example, a cis well may be fluidically connected to a trans well or a plurality of trans wells, such that at least a portion of an electrolyte may flow freely between the connected wells. The two spatial regions may be in fluid communication through a nanopore, or through one or more valves, restrictors, or other fluidic components that are to control or regulate a flow of fluid through a system.

As used herein, the term "interstitial region" refers to an area in a substrate/solid support or a membrane, or an area on a surface that separates other areas, regions, features associated with the support or membrane or surface. For example, an interstitial region of a membrane can separate one nanopore of an array from another nanopore of the array. For another example, an interstitial region of a substrate can separate one trans well from another trans well. The two areas that are separated from each other can be discrete, i.e., lacking physical contact with each other. In many examples, the interstitial region is continuous whereas the areas are discrete, for example, as is the case for a plurality of nanopores defined in an otherwise continuous membrane, or for a plurality of wells defined in an otherwise continuous support. The separation provided by an interstitial region can be partial or full separation. Interstitial regions may have a surface material that differs from the surface material of the features defined in the surface. For example, the surface material at the interstitial regions may be a lipid material, and a nanopore formed in the lipid material can have an amount or concentration of polypeptide that exceeds the amount or concentration present at the interstitial regions. In some examples, the polypeptide may not be present at the interstitial regions.

As used herein, the term "membrane" refers to a non-permeable or semi-permeable barrier or other sheet that separates two liquid/gel chambers (e.g., a cis well and a trans well) which can contain the same compositions or different compositions therein. The permeability of the membrane to any given species depends upon the nature of the membrane. In some examples, the membrane may be non-permeable to ions, to electric current, and/or to fluids. For example, a lipid membrane may be impermeable to ions (i.e., does not allow any ion transport therethrough), but may be at least partially permeable to water (e.g., water diffusivity ranges from about 40 μm/s to about 100 μm/s). For another example, a solid state membrane, such as silicon nitride, may be impermeable to ions, electric charge, and fluids (i.e., the diffusion of all of these species is zero). Any membrane may be used in accordance with the present disclosure, so long as the membrane can include a transmembrane nanopore opening and can maintain a potential difference across the membrane. The membrane may be a monolayer or a multilayer membrane. A multilayer membrane includes several layers, each of which is a non-permeable or semi-permeable material.

The membrane may be formed of materials of biological or non-biological origin. A material that is of biological origin refers to material derived from or isolated from a biological environment such as an organism or cell, or a synthetically manufactured version of a biologically available structure.

An example membrane that is made from the material of biological origin includes a monolayer formed by a bola-lipid. Another example membrane that is made from the material of biological origin includes a lipid bilayer. Suitable lipid bilayers include, for example, a membrane of a cell, a membrane of an organelle, a liposome, a planar lipid bilayer, and a supported lipid bilayer. A lipid bilayer can be formed, for example, from two opposing layers of phospholipids, which are arranged such that their hydrophobic tail groups face towards each other to form a hydrophobic interior, whereas the hydrophilic head groups of the lipids face outwards towards the aqueous environment on each side of the bilayer. Lipid bilayers also can be formed, for example, by a method in which a lipid monolayer is carried on an aqueous solution/air interface past either side of an aperture which is perpendicular to that interface. The lipid is normally added to the surface of an aqueous electrolyte solution by first dissolving it in an organic solvent and then allowing a drop of the solvent to evaporate on the surface of the aqueous solution on either side of the aperture. Once the organic solvent has at least partially evaporated, the solution/air interfaces on either side of the aperture are physically moved up and down past the aperture until a bilayer is formed. Other suitable methods of bilayer formation include tip-dipping, painting bilayers, and patch-clamping of liposome bilayers. Any other methods for obtaining or generating lipid bilayers may also be used.

A material that is not of biological origin may also be used as the membrane. Some of these materials are solid state materials and can form a solid state membrane, and others of these materials can form a thin liquid film or membrane. The solid state membrane can be a monolayer, such as a coating or film on a supporting substrate (i.e., a solid support), or a free-standing element. The solid state membrane can also be a composite of multilayered materials in a sandwich configuration. Any material not of biological origin may be used, so long as the resulting membrane can include a transmembrane nanopore opening and can maintain a potential difference across the membrane. The membranes may include organic materials, inorganic materials, or both. Examples of suitable solid state materials include, for example, microelectronic materials, insulating materials (e.g., silicon nitride ($Si_3N_4$), aluminum oxide ($Al_2O_3$), and silicon oxide (SiO)), some organic and inorganic polymers (e.g., polyamide, plastics, such as polytetrafluoroethylene (PTFE), or elastomers, such as two-component addition-cure silicone rubber), and glasses. In addition, the solid state membrane can be made from a monolayer of graphene, which is an atomically thin sheet of carbon atoms densely packed into a two-dimensional honeycomb lattice, a multi-layer of graphene, or one or more layers of graphene mixed with one or more layers of other solid state materials. A graphene-containing solid state membrane can include at least one graphene layer that is a graphene nanoribbon or graphene nanogap, which can be used as an electrical sensor to characterize the target polynucleotide. The solid state membrane can be made by any suitable method. As examples, the graphene membrane can be prepared through either chemical vapor deposition (CVD) or exfoliation from graphite. Examples of suitable thin liquid film materials that may be used include diblock copolymers, triblock copolymers, such as amphiphilic PMOXA-PDMS-PMOXA ABA triblock copolymers.

As used herein, the term "nanopore" is intended to mean a hollow structure discrete from and extending across the membrane that permits ions, electric current, and/or fluids to cross from one side of the membrane to the other side of the membrane. For example, a membrane that inhibits the passage of ions or water soluble molecules can include a nanopore structure that extends across the membrane to permit the passage of the ions or water soluble molecules from one side of the membrane to the other side of the membrane. The diameter of the nanopore can vary along its length (i.e., from one side of the membrane to the other side of the membrane), but at any point is on the nanoscale (i.e., from about 1 nm to about 100 nm). Examples of the nanopore include, for example, biological nanopores, solid state nanopores, and biological and solid state hybrid nanopores.

As used herein, the term "biological nanopore" is intended to mean a nanopore whose structure portion is made from materials of biological origin. Biological origin refers to a material derived from or isolated from a biological environment such as an organism or cell, or a synthetically manufactured version of a biologically available structure. Biological nanopores include, for example, polypeptide nanopores and polynucleotide nanopores.

As used herein, the term "polypeptide nanopore" is intended to mean a polypeptide that extends across the membrane, and permits ions, electric current, and/or fluids to flow from one side of the membrane to the other side of the membrane. A polypeptide nanopore can be a monomer, a homopolymer, or a heteropolymer. Structures of polypeptide nanopores include, for example, an α-helix bundle nanopore and a β-barrel nanopore. Example polypeptide nanopores include α-hemolysin, *Mycobacterium smegmatis* porin A (MspA), gramicidin A, maltoporin, OmpF, OmpC, PhoE, Tsx, F-pilus, etc. *Mycobacterium smegmatis* porin A (MspA) is a membrane porin produced by Mycobacteria, which allows hydrophilic molecules to enter the bacterium.

MspA forms a tightly interconnected octamer and transmembrane beta-barrel that resembles a goblet and contains a central channel/pore.

A polypeptide nanopore can be synthetic. A synthetic polypeptide nanopore includes a protein-like amino acid sequence that does not occur in nature. The protein-like amino acid sequence may include some of the amino acids that are known to exist but do not form the basis of proteins (i.e., non-proteinogenic amino acids). The protein-like amino acid sequence may be artificially synthesized rather than expressed in an organism and then purified/isolated.

As used herein, the term "polynucleotide nanopore" is intended to include a polynucleotide that extends across the membrane, and permits ions, electric current, and/or fluids to flow from one side of the membrane to the other side of the membrane. A polynucleotide pore can include, for example, a polynucleotide origami (e.g., nanoscale folding of DNA to create the nanopore).

Also as used herein, the term "solid state nanopore" is intended to mean a nanopore whose structure portion includes materials of non-biological origin (i.e., not of biological origin). A solid-state nanopore can be formed of an inorganic or organic material. Solid state nanopores include, for example, silicon nitride nanopores, silicon dioxide ($SiO_2$) nanopores, and graphene nanopores.

The nanopores disclosed herein may be hybrid nanopores. A "hybrid nanopore" refers to a nanopore including materials of both biological and non-biological origins. An example of a hybrid nanopore includes a polypeptide-solid state hybrid nanopore and a polynucleotide-solid state nanopore.

As used herein, the term "nanopore sequencer" refers to any of the devices disclosed herein that can be used for nanopore sequencing. In the examples disclosed herein, during nanopore sequencing, the nanopore is immersed in example(s) of the electrolyte disclosed herein and a potential difference is applied across the membrane. In an example, the potential difference is an electric potential difference or an electrochemical potential difference. An electrical potential difference can be imposed across the membrane via a voltage source that injects or administers current to at least one of the ions of the electrolyte contained in the cis well or one or more of the trans wells. An electrochemical potential difference can be established by a difference in ionic composition of the cis and trans wells in combination with an electrical potential. The different ionic composition can be, for example, different ions in each well or different concentrations of the same ions in each well.

The application of the potential difference across the nanopores may force the translocation of a nucleic acid through the nanopore. One or more signals are generated that correspond to the translocation of the nucleotide through the nanopore. Accordingly, as a target polynucleotide, or as a mononucleotide or a probe derived from the target polynucleotide or mononucleotide, transits through the nanopore, the current across the membrane changes due to base-dependent (or probe dependent) blockage of the constriction, for example. The signal from that change in current can be measured using any of a variety of methods. Each signal is unique to the species of nucleotide(s) (or probe) in the nanopore, such that the resultant signal can be used to determine a characteristic of the polynucleotide. For example, the identity of one or more species of nucleotide(s) (or probe) that produces a characteristic signal can be determined.

As used herein, a "nucleotide" includes a nitrogen containing heterocyclic base, a sugar, and one or more phosphate groups. Nucleotides are monomeric units of a nucleic acid sequence. Examples of nucleotides include, for example, ribonucleotides or deoxyribonucleotides. In ribonucleotides (RNA), the sugar is a ribose, and in deoxyribonucleotides (DNA), the sugar is a deoxyribose, i.e., a sugar lacking a hydroxyl group that is present at the 2' position in ribose. The nitrogen containing heterocyclic base can be a purine base or a pyrimidine base. Purine bases include adenine (A) and guanine (G), and modified derivatives or analogs thereof. Pyrimidine bases include cytosine (C), thymine (T), and uracil (U), and modified derivatives or analogs thereof. The C-1 atom of deoxyribose is bonded to N-1 of a pyrimidine or N-9 of a purine. The phosphate groups may be in the mono-, di-, or tri-phosphate form. These nucleotides are natural nucleotides, but it is to be further understood that non-natural nucleotides, modified nucleotides or analogs of the aforementioned nucleotides can also be used.

As used herein, the term "signal" is intended to mean an indicator that represents information. Signals include, for example, an electrical signal and an optical signal. The term "electrical signal" refers to an indicator of an electrical quality that represents information. The indicator can be, for example, current, voltage, tunneling, resistance, potential, voltage, conductance, or a transverse electrical effect. An "electronic current" or "electric current" refers to a flow of electric charge. In an example, an electrical signal may be an electric current passing through a nanopore, and the electric current may flow when an electric potential difference is applied across the nanopore.

The term "substrate" refers to a rigid, solid support that is insoluble in aqueous liquid and is incapable of passing a liquid absent an aperture, port, or other like liquid conduit. In the examples disclosed herein, the substrate may have wells or chambers defined therein. Examples of suitable substrates include glass and modified or functionalized glass, plastics (including acrylics, polystyrene and copolymers of styrene and other materials, polypropylene, polyethylene, polybutylene, polyurethanes, polytetrafluoroethylene (PTFE) (such as TEFLON® from Chemours), cyclic olefins/cyclo-olefin polymers (COP) (such as ZEONOR® from Zeon), polyimides, etc.), nylon, ceramics, silica or silica-based materials, silicon and modified silicon, carbon, metals, inorganic glasses, and optical fiber bundles.

The terms top, bottom, lower, upper, on, etc. are used herein to describe the nanopore sequencer and/or the various components of the nanopore sequencer. It is to be understood that these directional terms are not meant to imply a specific orientation, but are used to designate relative orientation between components. The use of directional terms should not be interpreted to limit the examples disclosed herein to any specific orientation(s).

As used herein, the term "well" and "chamber" are used synonymously, and refer to a discrete feature defined in the sequencer that can contain a fluid (e.g., liquid, gel, gas). A "cis well" is a common chamber that contains or is partially defined by a cis electrode, and is also fluidically connected to each of a plurality of trans wells through a respective nanopore. A sequencer may have one cis well or multiple cis wells. Each "trans well" is a single chamber that contains or is partially defined by its own trans electrode, and is also fluidically connected to one cis well. Each trans well is electrically isolated from each other trans well, and the respective trans electrodes are connected to respective amplifiers (e.g., Axopatch 200B amplifiers) to amplify electrical signals passing through respective nanopores associated with each of the trans wells. The cross-section of a well taken parallel to a surface of a substrate at least partially defining the well can be curved, square, polygonal, hyperbolic, conical, angular, etc.

The aspects and examples set forth herein and recited in the claims can be understood in view of the above definitions.

Referring now to FIG. 1, an example of a nanopore sequencer 10 is depicted. The nanopore sequencer 10 includes a cis well 14, a trans well 16, a nanopore 18 fluidically connecting the cis well 14 and the trans well 16, and a modified electrolyte 20 in the cis well 14, or the trans well 16, or the cis and trans wells 14, 16. In examples where the modified electrolyte 20 is in one of the cis well 14 or the trans well 16, a non-modified electrolyte 22 may be present in the other of the trans well 16 or the cis well 14.

As shown in FIG. 1, a substrate 12 may include a plurality of trans wells 16 defined therein. Each of the trans wells 16 may be fluidically connected to the common cis well 14 by a respective nanopore 18. While one common cis well 14 is shown in FIG. 1, it is to be understood that the sequencer 10 may include several cis wells 14 that are fluidically isolated from one another and are fluidically connected to respective sets of trans wells 16 defined in the substrate 12. Multiple cis wells 14 may be desirable, for example, in order to enable the measurement of multiple samples on a single substrate 12.

The fluid communication through the nanopore(s) 18 is indicated by the arrow in FIG. 1. Also, as shown in FIG. 1, a membrane 24 may be positioned on the substrate 12 between the cis well 14 and the trans well(s) 16, and the nanopore(s) 18 may be positioned in, and extend through the membrane 24 to establish the fluidic connection between the cis well 14 and the trans well(s) 16.

The cis well 14 is a fluid chamber that is defined on a portion of the substrate 12 by sidewall(s) 13 that are connected to the substrate 12. In some examples, the sidewall(s) 13 and the substrate 12 may be integrally formed such that they 13, 12 are formed from a continuous piece of material (e.g., glass or plastic). In other examples, the sidewall(s) 13 and the substrate 12 may be separate components that are coupled to each other. In an example, the sidewall(s) are photo patternable polymers.

In the example shown in FIG. 1, the cis well 14 has interior walls 26, 26' that are defined by the sidewall(s) 13, an upper surface 28 that is defined by a cis electrode 30, and a lower surface 28' that is defined by the membrane 24. Thus, the cis well 14 is formed within the space defined by the cis electrode 30, the portion of the substrate 12, and the membrane 24. It is to be understood that the lower surface 28' has opening(s) through the nanopore(s) 18 that are positioned in the membrane 24. The cis well 14 may have any suitable dimensions. In an example, the cis well 14 ranges from about 1 mm×1 mm to about 5 mm×5 mm.

The cis electrode 30, whose interior surface is the upper surface 28 of the cis well 14, may be physically connected to the sidewall(s) 13. The cis electrode 30 may be physically connected to the sidewall(s) 13, for example, by an adhesive or another suitable fastening mechanism. The interface between the cis electrode 30 and the sidewall(s) 13 may seal the upper portion of the cis well 14.

The cis electrode 30 that is used depends, at least in part, upon the redox couple in the modified electrolyte 20. As examples, the cis electrode 30 may be gold (Au), platinum (Pt), carbon (C) (e.g., graphite, diamond, etc.), palladium (Pd), silver (Ag), copper (Cu), or the like. In an example, the cis electrode 30 may be a silver/silver chloride (Ag/AgCl) electrode.

The cis well 14 is capable of maintaining the modified electrolyte 20 or the non-modified electrolyte 22 in contact with the nanopore(s) 18. In an example, the cis well 14 is in contact with an array of nanopores 18, and thus is capable of maintaining the modified electrode 20 or the non-modified electrolyte 22 in contact with each of the nanopores 18 in the array.

As illustrated in FIG. 1, the nanopore sequencer 10 includes a plurality of trans wells 16. Each trans well 16 is a fluid chamber that is defined in a portion of the substrate 12. Generally, the trans wells 16 may extend through the thickness of the substrate 12 and may have openings at opposed ends (e.g., a top end 38 and a bottom end 40) of the substrate 12. In the example shown in FIG. 1, each trans well 16 has sidewalls 31, 31' that are defined by the substrate 12 and/or by interstitial regions 32 of the substrate 12, a lower surface 36 that is defined by a trans electrode 34, and an upper surface 36' that is defined by the membrane 24. Thus, each trans well 16 is formed within the space defined by the trans electrode 34, the other portion and/or interstitial regions 32 of the substrate 12, and the membrane 24. It is to be understood that the upper surface 36' has opening(s) through the nanopore(s) 18 positioned in the membrane 24.

The trans electrode 34, whose interior surface is the lower surface 36 of the trans well 16, may be physically connected to the substrate 12 (e.g., to the interstitial regions 32 or to an interior wall of the substrate 12). The trans electrode 34 may be fabricated in the process of forming the substrate 12 (e.g., during the formation of the trans wells 16). Microfabrication techniques that may be used to form the substrate 12 and the trans electrode 34 include lithography, metal deposition and liftoff, dry and/or spin on film deposition, etching, etc. The interface between the trans electrode 34 and the substrate 12 may seal the lower portion of the trans well 16.

The trans electrode 34 that is used depends, at least in part, upon the redox couple in the modified electrolyte 20. As examples, the trans electrode 34 may be may be gold (Au), platinum (Pt), carbon (C) (e.g., graphite, diamond, etc.), palladium (Pd), silver (Ag), copper (Cu), or the like. In an example, the trans electrode 34 may be a silver/silver chloride (Ag/AgCl) electrode.

Many different layouts of the trans wells 16 may be envisaged, including regular, repeating, and non-regular patterns. In an example, the trans wells 16 are disposed in a hexagonal grid for close packing and improved density. Other layouts may include, for example, rectilinear (i.e., rectangular) layouts, triangular layouts, and so forth. As examples, the layout or pattern can be an x-y format of trans wells 16 that are in rows and columns. In some other examples, the layout or pattern can be a repeating arrangement of trans wells 16 and/or interstitial regions 32. In still other examples, the layout or pattern can be a random arrangement of trans wells 16 and/or interstitial regions 32. The pattern may include spots, posts, stripes, swirls, lines, triangles, rectangles, circles, arcs, checks, plaids, diagonals, arrows, squares, and/or cross-hatches.

The layout may be characterized with respect to the density of the trans wells 16 (i.e., number of trans wells 16 in a defined area of the substrate 12). For example, the trans wells 16 may be present at a density ranging from about 10 wells per $mm^2$ to about 1,000,000 wells per $mm^2$. The density may be tuned to different densities including, for example, a density of at least about 10 per $mm^2$, about 5,000 per $mm^2$, about 10,000 per $mm^2$, about 0.1 million per $mm^2$, or more. Alternatively or additionally, the density may be tuned to be no more than about 1,000,000 wells per $mm^2$, about 0.1 million per $mm^2$, about 10,000 per $mm^2$, about 5,000 per mm², or less. It is to be further understood that the density of the trans wells 16 in the support 12 can be between one of the lower values and one of the upper values selected from the ranges above.

The layout may also or alternatively be characterized in terms of the average pitch, i.e., the spacing from the center of a nanopore 18 to the center of an adjacent nanopore 18 (center-to-center spacing). The pattern can be regular such that the coefficient of variation around the average pitch is small, or the pattern can be non-regular in which case the coefficient of variation can be relatively large. In an example, the average pitch may range from about 100 nm to about 500 µm. The average pitch can be, for example, at least about 100 nm, about 5 µm, about 10 µm, about 100 µm, or more. Alternatively or additionally, the average pitch can be, for example, at most about 500 µm, about 100 µm, about 50 µm, about 10 µm, about 5 µm, or less. The average pitch for an example array including a particular pattern of nanopores 18 can be between one of the lower values and one of the upper values selected from the ranges above. In an example, the array has an average pitch (center-to-center spacing) of about 10 µm.

The trans wells 16 may be micro wells (having at least one dimension on the micron scale, e.g., about 1 µm up to, but not including, 1000 µm) or nanowells (having at least one dimension on the nanoscale, e.g., about 10 nm up to, but not including, 1000 nm). Each well 16 may be characterized by its aspect ratio (e.g., width or diameter divided by depth or height in this example).

In an example, the aspect ratio of each trans well 16 may range from about 1:1 to about 1:5. In another example, the aspect ratio of each trans well 16 may range from about 1:10 to about 1:50. In an example, the aspect ratio of the trans well 16 is about 3.3.

The depth/height and width/diameter may be selected in order to obtain a desirable aspect ratio. The depth/height of each trans well 16 can be at least about 0.1 µm, about 1 µm, about 10 µm, about 100 µm, or more. Alternatively or additionally, the depth can be at most about 1,000 µm, about 100 µm, about 10 µm, about 1 µm, about 0.1 µm, or less. The width/diameter of each trans well 16 can be at least about 50 nm, about 0.1 µm, about 0.5 µm, about 1 µm, about 10 µm, about 100 µm, or more. Alternatively or additionally, the width/diameter can be at most about 1,000 µm, about 100 µm, about 10 µm, about 1 µm, about 0.5 µm, about 0.1 µm, about 50 nm, or less.

Each trans well 16 has an opening (e.g., that faces the cis well 14) that is large enough to accommodate at least a portion of the membrane 24 and the nanopore 18 that is associated therewith. For example, an end of the nanopore 18 may extend through the membrane 24 and into the opening of the trans well 16.

The cis well 14 and the trans wells 16 may be fabricated using a variety of techniques, including, for example, photolithography, nanoimprint lithography, stamping techniques, embossing techniques, molding techniques, microetching techniques, etc. As will be appreciated by those in the art, the technique used will depend on the composition and shape of the support 12 and the sidewall(s) 13. In an example, the cis well 14 may be defined by sidewall(s) 13 at an end 38 of the support 12, and the trans wells 16 may be defined through the support 12.

The membrane 24 may be any of the non-permeable or semi-permeable materials described herein. The membrane 24 is positioned between the cis well 14 and the trans wells 16, and thus provides a barrier between the wells 14, 16. The membrane may be positioned on the interstitial regions 32 of the substrate 12.

The nanopore(s) 18 may be any of the biological nanopores, solid state nanopores, and hybrid nanopores described herein. As mentioned herein, each nanopore 18 fluidically connects a respective one of the trans wells 16 to the cis well 14. As such, the ratio of nanopores 18 to trans wells 16 is 1:1.

The nanopore 18 has two open ends and a hollow core or hole that connects the two open ends. When inserted into the membrane 24, one of the open ends of the nanopore 18 faces the cis well 14 and the other of the open ends of the nanopore 18 faces the trans well 16 and is aligned with at least a portion of the opening of trans well 16. The hollow core of the nanopore 18 enables the fluidic connection between the wells 14, 16. The diameter of the hollow core may range from about 1 nm up to 1 µm, and may vary along the length of the nanopore 18. In some examples, the open end that faces the cis well 14 may be larger than the open end that faces the trans well 16. In other examples, the open end that faces the cis well 14 may be smaller than the open end that faces the trans well 16.

The nanopore(s) 18 may be inserted into the membrane 24, or the membrane 24 may be formed around the nanopore(s) 18. In an example, the nanopore 18 may insert itself into a formed lipid bilayer (one example of the membrane 24) For example, a nanopore 18 in its monomeric form or polymeric form (e.g., an octamer) may insert itself into the lipid bilayer and assemble into a transmembrane pore. In another example, the nanopore 18 may be added to a grounded side of a lipid bilayer at a desirable concentration where it will insert itself into the lipid bilayer. In still another example, the lipid bilayer may be formed across an aperture in a polytetrafluoroethylene (PTFE) film and positioned between the cis and trans wells. The nanopore may be added to the grounded cis compartment, and may insert itself into the lipid bilayer at the area where the PTFE aperture is formed. In yet a further example, the nanopore 18 may be tethered to a solid support (e.g., silicon, silicon oxide, quartz, indium tin oxide, gold, polymer, etc.). A tethering molecule, which may be part of the nanopore 18 itself or may be attached to the nanopore 18, may attach the nanopore 18 to the solid support. The attachment via the tethering molecule may be such that a single pore 18 is immobilized (e.g., between two chambers/wells). A lipid bilayer may then be formed around the nanopore 18.

As mentioned above, some examples of the nanopore sequencer 10 include the modified electrolyte 20 in both the cis well 14 and the trans wells 16. In other examples, the modified electrolyte 20 is in either the trans wells 16 or the cis well 14. As such, the nanopore sequencer 10 shown in FIG. 1 also may include two electrolytes, namely the modified electrolyte 20 and the non-modified electrolyte 22.

The modified electrolyte 20 includes an electrolyte and a cation complexing agent. The electrolyte may be any electrolyte that is capable of dissociating into counter ions (a cation and its associated anion). As examples, the electrolyte may be any electrolyte that is capable of dissociating into a potassium cation ($K^+$) or a sodium cation ($Na^+$). This type of electrolyte includes a potassium cation and an associated anion, or a sodium cation and an associated anion, or combinations thereof. Examples of potassium-containing electrolytes include potassium chloride (KCl), potassium ferricyanide ($K_3[Fe(CN)_6]\cdot 3H_2O$ or $K_4[Fe(CN)_6]\cdot 3H_2O$), or other potassium-containing electrolytes (e.g., bicarbonate ($KHCO_3$) or phosphates (e.g., $KH_2PO_4$, $K_2HPO_4$, $K_3PO_4$). Examples of sodium-containing electrolytes include sodium chloride (NaCl) or other sodium-containing electrolytes, such as sodium bicarbonate ($NaHCO_3$), sodium phosphates (e.g., $NaH_2PO_4$, $Na_2HPO_4$ or $Na_3PO_4$). As another example, the electrolyte may be any electrolyte that is capable of dissociating into a ruthenium-containing cation (e.g., ruthenium hexamine, such as $[Ru(NH_3)_6]^{2+}$ or $[Ru(NH_3)_6]^{3+}$). Electrolytes that are capable of dissociating into a lithium cation ($Li^+$), a rubidium cation ($Rb^+$), a magnesium cation ($Mg^+$), or a calcium cation ($Ca^+$) may also be used.

The cation complexing agent used in the modified electrolyte 20 depends upon the cation of the electrolyte that is used. The cation complexing agent is included to complex the cation of the electrolyte, and thus a diameter of a center cavity of the cation complexing agent is selected to match the size of the cation. By "match," it is meant the cation can fit within the center cavity, and that the atoms of the cation complexing agent can complex with the cation.

Examples of suitable cation complexing agents include crown ethers, calixarenes, and valinomycin. Examples of suitable crown ethers include:

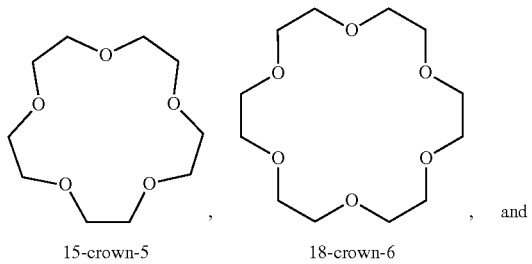

15-crown-5   18-crown-6

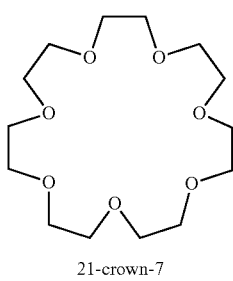

21-crown-7

It is to be understood that derivatives of these crown ethers may also be used, such as benzo- or dibenzo-15-crown-5, benzo- or dibenzo-18-crown-6, benzo- or dibenzo-21-crown-7, dicyclohexano-18-crown-6, dicyclohexano-21-crown-7, or the like. Azacrowns (e.g., aza-15-crown-5) or thiacrowns may also be used. Examples of suitable calixarenes include and $C_3Cal-5$, $C_3Cal-6$, and calix[4]arene tetraesters. Valinomycin is shown below:

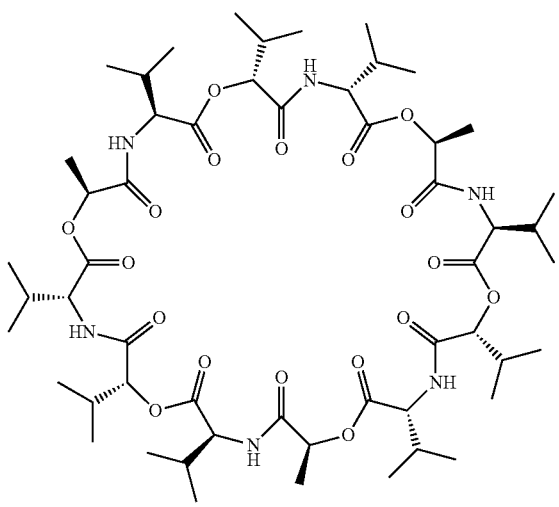 [SMILES: CC(C)[C@@H]1NC(=O)[C@H](C)OC(=O)[C@@H](C(C)C)NC(=O)[C@@H](C(C)C)OC(=O)[C@H](C(C)C)NC(=O)[C@H](C)OC(=O)[C@@H](C(C)C)NC(=O)[C@@H](C(C)C)OC(=O)[C@H](C(C)C)NC(=O)[C@H](C)OC(=O)[C@@H](C(C)C)NC(=O)[C@@H](C(C)C)OC1=O]

Examples of matching cations and cation complexing agents are shown in Table 1.

TABLE 1

| Cation | Cation Diameter | Crown Ethers (center cavity diameter) | Calixarenes | Valinomycin |
|---|---|---|---|---|
| $K^+$ | ~266 pm | 18-crown-6 (from about 260 pm to about 320 pm) | $C_3Cal-5$ $C_3Cal-6$ | Can complex both, but has greater selectively for $K^+$ over $Na^+$ |
| $Na^+$ | from about 194 pm to about 204 pm | 15-crown-5 (from about 170 pm to about 220 pm) | Calix[4]arene tetraesters | |

The amount of the cation complexing agent in the modified electrolyte 20 may vary depending, at least in part, upon the affinity of the complexing agent for the cation. Taking into account this affinity, the cation complexing agent may be used in any suitable amount that will result in the complexation of at least 99% of the available cation. Generally, the molar concentration of the cation complexing agent may range from greater than 0 mM to about 1M. In an example, 18-crown-6 may be used in a potassium-containing electrolyte in a molar concentration ranging from about 50 mM to about 500 mM. In a more specific example, 18-crown-6 may be used in a potassium-containing electrolyte in a molar concentration of about 300 mM. In another example, calixarenes may be used in a potassium-containing or sodium-containing electrolyte in a molar concentration ranging from greater than 0 mM to about 20 mM. Any of the concentrations used may depend upon the solubility of the cation complexing agent in the electrolyte.

The non-modified electrolyte 22 includes the same electrolyte as the modified electrolyte 20, but without the cation complexing agent. As such, the non-modified electrolyte does not include the cation complexing agent.

When the modified electrolyte 20 is introduced into the cis well 14 and the trans wells 16, the non-modified electrolyte 22 is not used. When the modified electrolyte 20 is introduced into the cis well 14, the non-modified electrolyte may be introduced into the trans wells 16. When the non-modified electrolyte 22 is introduced into the cis well 14, the modified electrolyte may be introduced into the trans wells 16.

Whichever well 14 and/or 16 the modified electrolyte 20 is introduced into, it is to be understood that the cation complexing agent will complex available electrolyte cations within that well 14 and/or 16, and thus will render the cations too bulky to translocate out of that well 14 and/or 16 and through the nanopores(s) 18. The complexed cation(s) have a diameter that is nearly identical to (e.g., within about 5% of), or larger than, at least one of the open ends of the nanopore(s) 18. For example, the complex of $K^+$ and 18-crown-6 has a diameter of about 1.15 nm, and an MspA nanopore has a hollow center diameter (at its smallest section) of about 1.2 nm. The complexed cation will not be able to fit through the nanopores(s) 18, and thus cation transport through the nanopore(s) 18 will be suppressed during operation of the nanopore sequencer 10. By limiting the cation transport, the anions of the electrolyte will be forced to make up the ionic current difference, thus at least reducing the imbalance between the anion supply and the anion consumption at the trans electrode 34.

Figure 2:
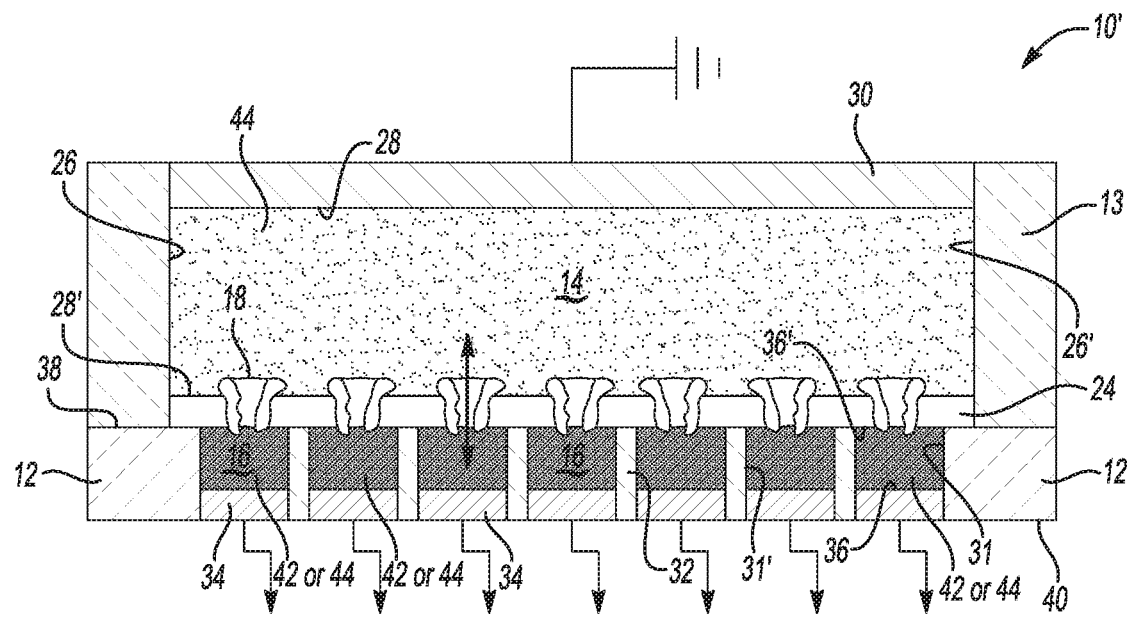
FIG. 2 is a schematic and partially cross-sectional view of another example of the nanopore sequencer disclosed herein.
Figure 3:
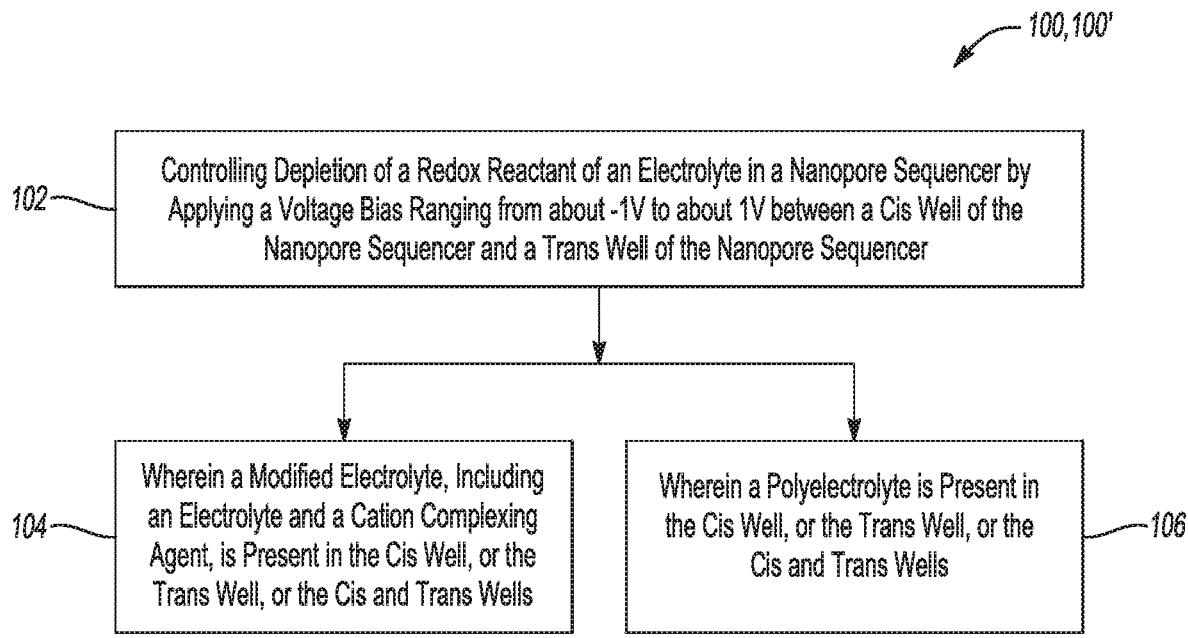
FIG. 3 is a flow diagram illustrating two examples of the method disclosed herein, one involving the nanopore sequencer of FIG. 1, and another involving the nanopore sequencer of FIG. 2.

Referring now to FIG. 3, examples of a method 100, 100' utilizing examples of the nanopore sequencers 10, 10' (the latter of which is shown in FIG. 2) are depicted. The example of the method 100 involving the nanopore sequencer 10 includes reference numerals 102 and 104. As shown at reference numeral 102, the method 100 involves controlling depletion of a redox reactant of an electrolyte in a nanopore sequencer 10 by applying a voltage bias ranging from about −1 V to about 1 V between a cis well 14 of the nanopore sequencer 10 and a trans well 16 of the nanopore sequencer 10, and as shown at reference numeral 104, a modified electrolyte 20, including an electrolyte and a cation complexing agent, is present in the cis well 14, or the trans well 16, or the cis and trans wells 14, 16. The voltage bias that is applied may depend upon the location of the modified electrolyte 20, e.g., when used in combination with the non-modified electrolyte 22. Any voltage bias within the given range may be applied when the modified electrolyte 20 is present in each of the wells 14, 16. This is due to the fact that ion motion is uni-directional, and thus complexed ions positioned on one side of the membrane 24 when a particular bias is applied will not affect current transport. For example, when a negative voltage bias is applied, the complexed ions in the trans well 16 do not affect current transport.

In an example, complexation of a cation (e.g., $K^+$) with a crown ether mitigates cation transport through the nanopore by reducing the current that flows by a factor of about 2× (2 times). The reduction in current flow may range from about 1× to about 3×.

In some examples, the method 100 may also include providing the nanopore sequencer 10 with the modified electrolyte 20 in each of the cis well 14 and the trans wells 16. In other examples, the method 100 may also include providing the nanopore sequencer 10 with the modified electrolyte 20 in one of the cis well 14 or the trans well 16 and with the electrolyte without the cation complexing agent (i.e., the non-modified electrolyte 22) in the other of the trans well 16 or the cis well 14.

The method 100 may also include incorporating the cation complexing agent into the electrolyte to form the modified electrolyte 20, introducing the modified electrolyte 20 to one of the cis well 14 or the trans well 16, and introducing the electrolyte without the cation complexing agent (i.e., the non-modified electrolyte 22) in the other of the trans well 16 or the cis well 14. As described herein, the concentration of the cation complexing agent may be varied, depending, at least in part, upon the affinity of the complexing agent for the cation.

The method 100 may be performed during a nanopore sequencing operation. The application of the electrical potential (i.e., the bias provided by the cis and trans electrodes 30, 34 as the current source) across the nanopore 18 forces the translocation of a nucleotide through the nanopore 18 along with the anions carrying the charge. Depending upon the bias, the nucleotide may be transported from the cis well 14 to the trans well 16, or from the trans well 16 to the cis well 14. As the nucleotide transits through the nanopores 18, the current across the barrier changes due, for example, to base-dependent blockage of the constriction, for example. The signal from that change in current can be measured using an amplifier, or another known signal detection device.

The range for the voltage can be selected from about −1 V to upwards of about 1 V. The voltage polarity is typically applied such that the negatively charged nucleic acid is electrophoretically driven into the nanopores 18. In some instances, the voltage can be reduced, or the polarity reversed, to facilitate appropriate function.

Referring now to FIG. 2, another example of the nanopore sequencer 10' is depicted. The nanopore sequencer 10' includes the cis well 14, the trans well 16, the nanopore 18 fluidically connecting the cis well 14 and the trans well 16, and a polyelectrolyte 42 in the cis well 14, or the trans well 16, or the cis and trans wells 14, 16. In examples where the polyelectrolyte 42 is in one of the cis well 14 or the trans well 16, an electrolyte 44 may be present in the other of the trans well 16 or the cis well 14.

As shown in FIG. 2, the substrate 12 may include a plurality of trans wells 16 defined therein and may be connected to sidewall(s) 13 which at least partially define the cis well 14. Each of the trans wells 16 may be fluidically connected to the common cis well 14 by a respective nanopore 18. While one common cis well 14 is shown in FIG. 2, it is to be understood that the sequencer 10' may include several cis wells 14 that are fluidically isolated from one another and are fluidically connected to respective sets of trans wells 16 defined in the substrate 12. Multiple cis wells 14 may be desirable, for example, in order to enable the measurement of multiple samples on a single substrate 12.

The fluid communication through the nanopore(s) 18 is indicated by the arrow in FIG. 2. Also as shown in FIG. 2, the membrane 24 may be positioned on the substrate 12 between the cis well 14 and the trans well(s) 16, and the nanopore(s) 18 may be positioned in and extend through the membrane 24 to establish the fluidic connection between the cis well 14 and the trans well(s) 16.

The cis well 14 and the trans well 16 of the nanopore sequencer 10' may be defined in the same manner and with the same configurations (e.g., dimensions, layouts, etc.) as described herein for the nanopore sequencer 10. Moreover, the cis electrode 30 and trans electrode(s) 34 may be physically connected, respectively, to the sidewall(s) 13 and substrate 12, and may respectively define the upper surface 28 of the cis well 14 and the lower surface 36 of the trans well(s) 16.

In the nanopore sequencer 10', the cis well 14 is capable of maintaining the electrolyte 44 or the polyelectrolyte 42 in contact with the nanopore(s) 18. In an example, the cis well 14 is in contact with an array of nanopores 18, and thus is capable of maintaining the electrolyte 44 or the polyelectrolyte 42 in contact with each of the nanopores 18 in the array. Also in the nanopore sequencer 10', each trans well 16 has an opening (e.g., that faces the cis well 14) that is large enough to accommodate at least a portion of the membrane 24 and the nanopore 18 that is associated therewith. For example, an end of the nanopore 18 may extend through the membrane 24 and into the opening of the trans well 16.

Any of the membranes 24 and the nanopores 18 described herein may be used for the nanopore sequencer 10'.

As mentioned above, some examples of the nanopore sequencer 10' include the polyelectrolyte 42 in both the cis well 14 and the trans wells 16. In other examples, the polyelectrolyte 42 is in either the trans wells 16 or the cis well 14. As such, the nanopore sequencer 10' shown in FIG. 2 may include two electrolytes, namely the polyelectrolyte 42 and the electrolyte 42. In the example of FIG. 2, the polyelectrolyte 42 is present in the trans wells 16, and the polyelectrolyte 42 or the electrolyte 44 is present in the cis well 14.

The polyelectrolyte 42 is a charged polymer, in a gel state, that can conduct current due to the coupling of ions of the opposite charge. In the example disclosed herein, the polyelectrolyte 42 has a positively charged backbone that couple with negatively charged ions (i.e., anions). Since the cations are part of the backbone of the polyelectrolyte 42, they may not readily translocate out of that well 16 or 14 and through the nanopores(s) 18. Examples of suitable polyelectrolytes 42 are selected from the group consisting of polydiallyldimethylammonium chloride (PDDA), an ionic form of polyethyleneimine (PEI), an ionic form of linear polyethyleneimine (LPEI), poly(allylamine hydrochloride) (PAH), and an ionic form of poly(4-vinylpyridine) (P4VP). Some example structures are shown below:

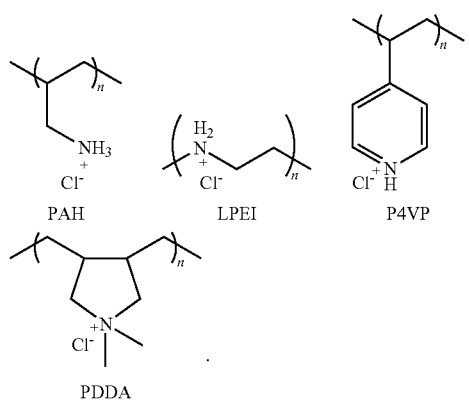

In these examples, the —$NH_2^+$ in the linear polyethyleneimine (LPEI) is coordinated to $Cl^-$, and the —$NH^+$ in the poly(4-vinylpyridine) (P4VP) is coordinated to $Cl^-$ (i.e., poly(4-vinylpyridine hydrochloride)). Another example of the ionic form of poly(4-vinylpyridine) (P4VP) is poly(4-vinylpyridine) methyl chloride, where the —$N^+CH_3$ in the poly(4-vinylpyridine) is coordinated to $Cl^-$. Anions other than chloride may be used, depending upon the electrolyte 44 that is to be used in the other of the wells 14, 16 and the nature of the electrochemical reaction on the trans electrode 34. It is desirable to preserve an electrolyte balance on the trans side, and so the ions consumed or produced by the trans electrode 34 should be matched to polyelectrolyte 42.

Although a polyelectrolyte 42 may not translate through the nanopore 18 as readily as free electrolyte, nanopores 18 have been shown to translocate charged polymers (e.g., polyethylene glycol (PEG), DNA). Therefore, non-linear polyelectrolytes 42 may be used to further impede the translocation of the polyelectrolyte 42 through the pore 18. For example, branched-PEI or a copolymer of a polyelectrolyte 42 and a monomer with cross-linkable groups.

When included in the trans well(s) 16, the polyelectrolyte 42 may also be able to improve the mechanical support and structural stability of the membrane 24 (e.g., a lipid bilayer).

When included, the electrolyte 42 may be any electrolyte that is capable of dissociating into counter ions (a cation and its associated anion). As examples, the electrolyte may be any electrolyte that is capable of dissociating into a potassium cation ($K^+$) or a sodium cation ($Na^+$). This type of electrolyte includes a potassium cation and an associated anion, or a sodium cation and an associated anion, or combinations thereof. Examples of potassium-containing electrolytes include potassium chloride (KCl), potassium ferricyanide ($K_3[Fe(CN)_6].3H_2O$ or $K_4[Fe(CN)_6].3H_2O$), or other potassium-containing electrolytes (e.g., bicarbonate ($KHCO_3$) or phosphates (e.g., $KH_2PO_4$, $K_2HPO_4$, $K_3PO_4$). Examples of sodium-containing electrolytes include sodium chloride (NaCl) or other sodium-containing electrolytes, such as sodium bicarbonate ($NaHCO_3$) or sodium phosphates (e.g., $NaH_2PO_4$, $Na_2HPO_4$, $Na_3PO_4$). As another example, the electrolyte may be any electrolyte that is capable of dissociating into a ruthenium-containing cation (e.g., ruthenium hexamine, such as $[Ru(NH_3)_6]^{2+}$ or $[Ru(NH_3)_6]^{3+}$). Electrolytes that are capable of dissociating into a lithium cation ($Li^+$), a rubidium cation ($Rb^+$), a magnesium cation ($Mg^+$), or a calcium cation ($Ca^+$) may also be used.

In an example of the nanopore sequencer 10', the polyelectrolyte 42 is present in both the cis and trans wells 14, 16, and the polyelectrolyte 42 is selected from the group consisting of polydiallyldimethylammonium chloride, an ionic form of polyethyleneimine, an ionic form of linear polyethyleneimine, poly(allylamine hydrochloride), and an ionic form of poly(4-vinylpyridine).

In another example of the nanopore sequencer 10', the polyelectrolyte 42 is selected from the group consisting of polydiallyldimethylammonium chloride, an ionic form of polyethyleneimine, an ionic form of linear polyethyleneimine, poly(allylamine hydrochloride), and an ionic form of poly(4-vinylpyridine); and the electrolyte 42 includes a potassium cation and an associated anion, or a sodium cation and an associated anion, or combinations thereof.

Referring again to FIG. 3, the example of the method 100' involving the nanopore sequencer 10' includes reference numerals 102 and 106. As shown at reference numeral 102, the method 100' involves controlling depletion of a redox reactant of an electrolyte in a nanopore sequencer 10' by applying a voltage bias ranging from about –1 V to about 1 V between a cis well 14 of the nanopore sequencer 10' and a trans well 16 of the nanopore sequencer 10', and as shown at reference numeral 106, a polyelectrolyte 42 is present in the cis well 14, or the trans well 16, or the cis and trans wells 14, 16. Any voltage bias may be applied that will preserve an electrolyte balance on the trans side.

In some examples, the method 100' may include providing the nanopore sequencer 10' with the polyelectrolyte 42 in the gel state in each of the cis well 14 and the trans wells 16. In other examples, the method 100' may also include providing the nanopore sequencer 10' with the polyelectrolyte 42 in the gel state in one of the cis well 14 or the trans well 16 and with the electrolyte 44 in the other of the trans well 16 or the cis well 14.

The method 100' may also include introducing the polyelectrolyte 42 (in the gel state) to the cis well 14, or the trans well(s) 16, or both the cis and trans wells 14, 16. When the polyelectrolyte 42 is in one of the wells 14 or 16, the method 100' may include introducing the electrolyte 44 in the other of the trans well 16 or the cis well 14.

The method 100' may be performed during a nanopore sequencing operation. The application of the electrical potential (i.e., the predetermined bias provided by the cis and trans electrodes 30, 34 as the current source) across the nanopore 18 forces the translocation of a nucleotide through the nanopore 18 along with the anions carrying the charge. Depending upon the bias, the nucleotide may be transported from the cis well 14 to the trans well 16, or from the trans well 16 to the cis well 14. As the nucleotide transits through the nanopores 18, the current across the barrier changes due, for example, to base-dependent blockage of the constriction, for example. The signal from that change in current can be measured using an amplifier, or another known signal detection device.

The range for the voltage can be selected from about −1V to upwards of about 1 V. The voltage polarity is typically applied such that the negatively charged nucleic acid is electrophoretically driven into the nanopores 18. In some instances, the voltage can be reduced, or the polarity reversed, to facilitate appropriate function.

Figure 4:
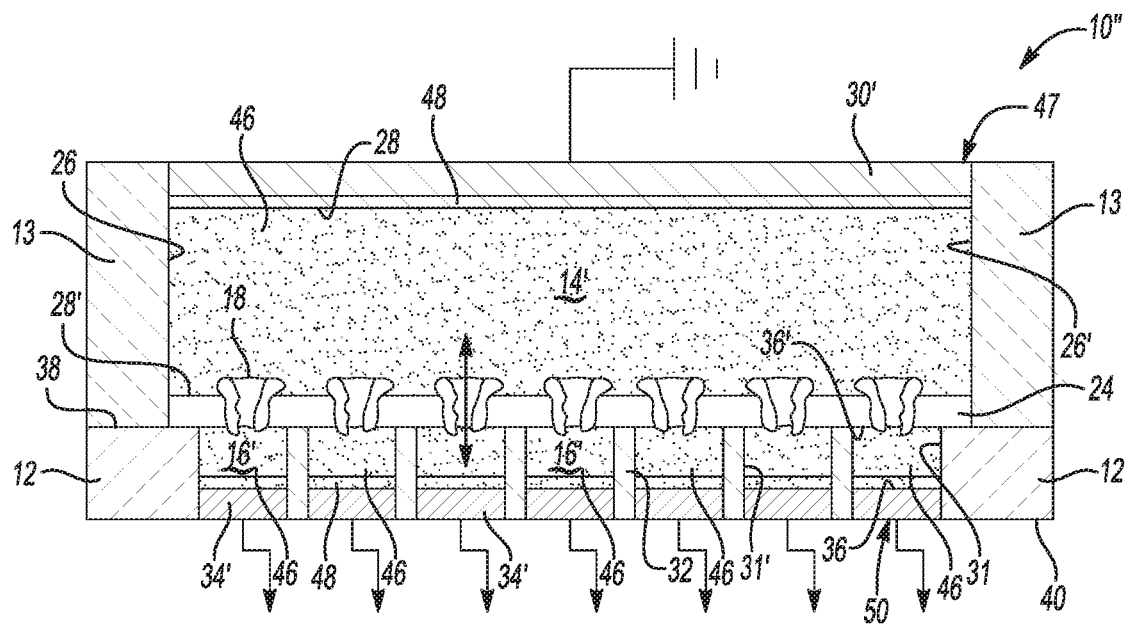
FIG. 4 is a schematic and partially cross-sectional view of still another example of the nanopore sequencer disclosed herein.

Referring now to FIG. 4, still another example of the nanopore sequencer 10" is depicted. The nanopore sequencer 10" includes the cis well 14', the trans well 16', and the nanopore 18 fluidically connecting the cis well 14' and the trans well 16', a cis well electrode structure 47 associated with the cis well 14' (the cis well electrode structure 47 including a first base electrode 30' and a redox solid 48 immobilized to the first base electrode 30'), a trans well electrode structure 50 associated with the trans well 16' (the trans well electrode structure 50 including a second base electrode 34' and the redox solid 48 immobilized to the second base electrode 34'), and an electrolyte 46 including a cation to be consumed or released in response to respective redox reactions at the cis well electrode structure 47 and the trans well electrode structure 50.

As shown in FIG. 4, the substrate 12 may include a plurality of trans wells 16' defined therein. Each of the trans wells 16' may be fluidically connected to the common cis well 14' by a respective nanopore 18. While one common cis well 14' is shown in FIG. 4, it is to be understood that the sequencer 10" may include several cis wells 14 that are fluidically isolated from one another and are fluidically connected to respective sets of trans wells 16' defined in the substrate 12. Multiple cis wells 14' may be desirable, for example, in order to enable the measurement of multiple samples on a single substrate 12.

The fluid communication through the nanopore(s) 18 is indicated by the arrow in FIG. 4. Also, as shown in FIG. 4, the membrane 24 may be positioned between the cis well 14' and the trans well(s) 16', and the nanopore(s) 18 may be positioned in and extend through the membrane 24 to establish the fluidic connection between the cis well 14 and the trans well(s) 16.

The cis well 14' and the trans well 16' of the nanopore sequencer 10' may be defined with the same configurations (e.g., dimensions, layouts, etc.) as described herein for the cis well 14 and the trans well 16 of the nanopore sequencer 10.

In this example, the cis well 14' has interior walls 26, 26' that are defined by sidewall(s) 13', an upper surface 28 that is defined by the redox solid 48 of the cis well electrode structure 47, and a lower surface 28' that is defined by the membrane 24. Thus, the cis well 14' is formed within the space defined by the redox solid 48 of the cis well electrode structure 47, the sidewall(s) 13', and the membrane 24.

The cis well electrode structure 47 may be physically connected to the sidewall(s) 13'. The cis well electrode structure 47 may be physically connected to the sidewall(s) 13', for example, by an adhesive or another suitable fastening mechanism. The interface between the cis well electrode structure 47 and the sidewall(s) 13' may seal the upper portion of the cis well 14'.

As mentioned above, the cis well electrode structure 47 includes the first base electrode 30' and the redox solid 48 immobilized to the first base electrode 30'. The first base electrode 30' may include, or in some instances consist of, a material selected from the group consisting of graphite, platinum, gold, silver, copper, carbon fiber, diamond, and palladium. The redox solid 48 may be selected from the group consisting of tetracyanoquinodimethane (TCNQ), Prussian blue (which may be used as a solid state electrode, e.g., in glucose sensors), and polypyrrole.

As illustrated in FIG. 4, the nanopore sequencer 10" includes a plurality of trans wells 16'. Each trans well 16' has an opening (e.g., that faces the cis well 14') that is large enough to accommodate at least a portion of the membrane 24 and the nanopore 18 that is associated therewith. For example, an end of the nanopore 18 may extend through the membrane 24 and into the opening of the trans well 16'.

Each trans well 16' is a fluid chamber that is defined in the substrate 12. In the example shown in FIG. 4, each trans well 16' has sidewalls 31, 31' that are defined by the substrate 12 and/or by interstitial regions 32 of the substrate 12, a lower surface 36 that is defined by the redox solid 48 of the trans well electrode structure 50, and an upper surface 36' that is defined by the membrane 24. Thus, each trans well 16' is formed within the space defined by the redox solid 48 of the trans well electrode structure 50, the other portion and/or interstitial regions 32 of the substrate 12, and the membrane 24. It is to be understood that the upper surface 36' has opening(s) through the nanopore(s) 18 positioned in the membrane 24.

The trans well electrode structure 50 may be physically connected to the substrate 12, and may be fabricated in the process of forming the substrate 12 (e.g., during the formation of the trans wells 16'). Microfabrication techniques that may be used to form the substrate 12 and the trans electrode 34' include lithography, metal deposition and liftoff, dry and/or spin on film deposition, etching, etc. The interface between the trans well electrode structure 50 and the substrate 12 may seal the lower portion of the trans well 16'.

As mentioned above, the trans well electrode structure 50 includes the second base electrode 34' and the redox solid 48 immobilized to the second base electrode 34'. The redox solid 48 on the second base electrode 34' is the same type of redox solid 48 immobilized on the first base electrode 30'. As such, the redox solid 48 on the second base electrode 34' may be selected from the group consisting of tetracyanoquinodimethane (TCNQ), Prussian blue, and polypyrrole. The base electrode 34' may be the same material as, or a different type of material than the base electrode 30'. As such, the second base electrode 34' may include, or in some instances, consist of a material selected from the group consisting of graphite, platinum, gold, silver, copper, carbon fiber, diamond, and palladium.

The redox solid 48 may be deposited on the respective base electrode 30', 34' using any suitable chemical or electrochemical deposition process. As an example, Prussian Blue may be deposited from aqueous solutions containing a mixture of ferric ($Fe^{3+}$) and ferricyanide ($[Fe^{3+}(CN)_6]^{3-}$) ions, either spontaneously in an open-circuit regime or by applying a reductive electrochemical driving force.

The thickness of the redox solid 48 may have a thickness ranging from about 10 nm to about 10 μm. As an example, a TCNQ redox solid may be a thick film ranging from about 100 nm to 5 μm. While several thickness ranges have been provided, it is to be understood that the thickness may depend, in part, on the given limits of the deposition process and the desired for a certain amount of redox solid to sustain long-term sequencer operation.

Any of the membranes 24 and the nanopores 18 described herein may be used for the nanopore sequencer 10".

The electrolyte 46 of the nanopore sequencer 10" may be any of the examples provided for the electrolyte 44. In short, the electrolyte 46 may be any electrolyte that is capable of dissociating into counter ions (a cation and its associated anion), where the cation is also capable of being released and consumed by the redox solid 48 on the base electrodes 30', 34'. In some instances, the electrolyte 46 is an aqueous solution of one of the electrolytes 44. In this example of the nanopore sequencer 10", the electrolyte 46 is present in the cis well 14' and the trans well(s) 16'. As such, the cis well 14' and the trans well(s) 16' are capable of maintaining the electrolyte 46 in contact with the nanopore(s) 18.

The redox solid 48 is redox active in the electrolyte 46 that is used in the cis well 14' and the trans well(s) 16' in a potential window where water does not breakdown. The examples of the redox solid 48 disclosed herein give rise to the redox reactions at relatively low potentials (e.g., −1 V to 1 V). The redox solid 48 may undergo a cathodic reaction (when exposed to a negative potential) that consumes a cation of the electrolyte 46 (e.g., Eqn. 1 below), and may undergo an anodic reaction (when exposed to a positive potential) that releases the cation to the electrolyte 46 (e.g., Eqn. 2 below). As an example, the redox reactions involving the electrode structures 47, 50 having a TCNQ redox solid 48 immobilized on the respective base electrodes 30', 34' involve:

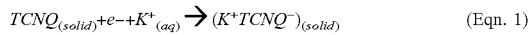

$$TCNQ_{(solid)} + e^- + K^+_{(aq)} \rightarrow (K^+TCNQ^-)_{(solid)} \quad \text{(Eqn. 1)}$$

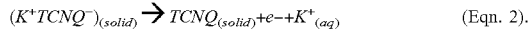

$$(K^+TCNQ^-)_{(solid)} \rightarrow TCNQ_{(solid)} + e^- + K^+_{(aq)} \quad \text{(Eqn. 2)}.$$

These reactions may be induced by the application of an appropriate potential so that cations (e.g., $K^+$) are released in the trans well(s) 16' and are consumed in the cis well 14'. This would eliminate anion depletion in the trans well(s) 16'.

Figure 5:
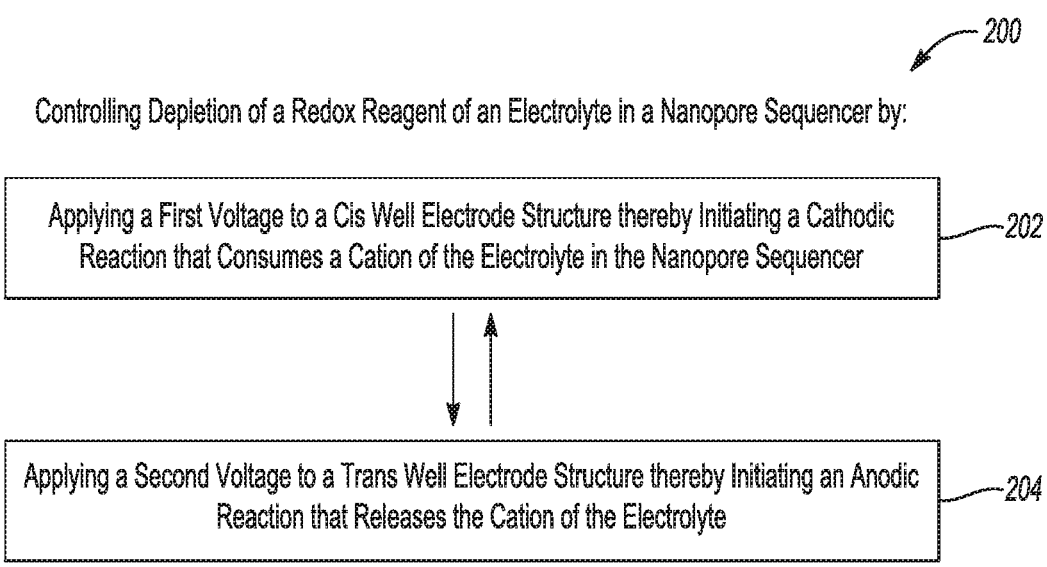
FIG. 5 is a flow diagram illustrating another example of the method disclosed herein involving the nanopore sequencer of FIG. 4.

Referring now to FIG. 5, the example of the method 200 involving the nanopore sequencer 10" involves controlling depletion of a redox reactant of an electrolyte 46 in the nanopore sequencer 10" by applying a first voltage to a cis well electrode structure 47 thereby initiating a cathodic reaction that consumes a cation of the electrolyte 46 in the nanopore sequencer 10" (as shown at reference numeral 202); and applying a second voltage to a trans well electrode structure 50, thereby initiating an anodic reaction that releases the cation of the electrolyte 46.

The method 200 may also include providing the nanopore sequencer 10" with the electrode structures 47, 50 and the electrolyte 46 in each of the cis well 14' and the trans well 16'. The method 200 may also include introducing electrolyte 46 in each of the cis well 14' and the trans well 16'.

The method 200 may be performed during a nanopore sequencing operation. The application of the electrical potential (i.e., the predetermined bias provided by the first and second electrode structures 47, 50 as the current source) across the nanopore 18 forces the translocation of a nucleotide through the nanopore 18 along with the cations and/or anions carrying the charge. Depending upon the bias, the nucleotide may be transported from the cis well 14' to the trans well 16', or from the trans well 16' to the cis well 14'. As the nucleotide transits through the nanopores 18, the current across the barrier changes due, for example, to base-dependent blockage of the constriction, for example. The signal from that change in current can be measured using an amplifier, or another known signal detection device.

The range for the voltage can be selected from about −1V to upwards of about 1.5 V. In an example, a suitable voltage range for operating the sequencer 10" using TCNQ as the redox solid 48 is from about 0.4 V to about 1.2 V. This corresponds to the voltage difference applied between the first and second base electrodes 30', 34'. The voltage polarity may be applied such that the negatively charged nucleic acid is electrophoretically driven into the nanopores 18. In some instances, the voltage can be reduced, or the polarity reversed, to facilitate appropriate function.

To further illustrate the present disclosure, examples are given herein. It is to be understood that these examples are provided for illustrative purposes and are not to be construed as limiting the scope of the present disclosure.

NON-LIMITING WORKING EXAMPLES

Example 1

Two nanopore sequencers (respectively referred to herein as "1" or "pore 1" and "2" or "pore 2") having a single cis well and a single trans well were prepared. Potassium chloride, without any crown ether added thereto, was introduced into the cis and trans wells of the sequencers 1, 2. Each of the nanopore sequencers 1, 2 included MspA nanopores positioned in a lipid bilayer membrane between the cis well and the trans well.

Figure 6A:
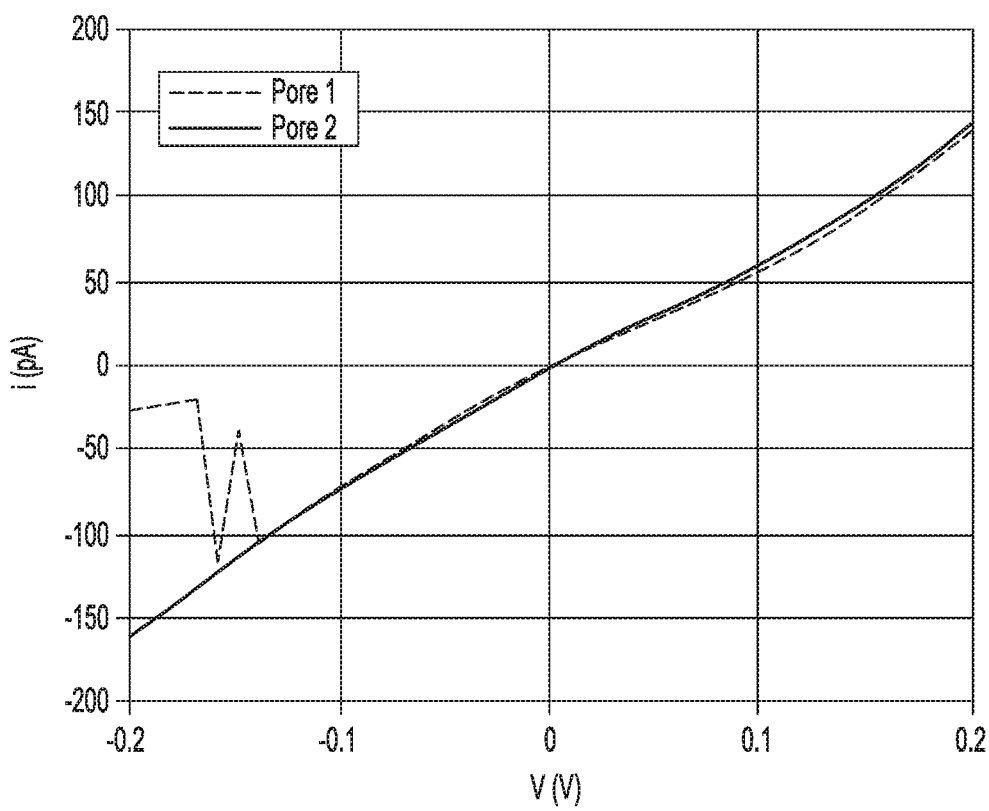
FIGS. 6A, 6B, and 6C are graphs illustrating current (i, pA) versus voltage (V) for A) two nanopore sequencers (1, 2) without a crown ether added, B) the nanopore sequencer (2) without the crown ether added and the nanopore sequencer (2) with the crown ether added in both the cis and trans wells, and C) the nanopore sequencer (2) without the crown ether added and the nanopore sequencer (2) from FIG. 6B after the crown ether was perfused from the cis chamber.

Various voltage potentials were applied across each of the nanopores in each of the nanopores sequencers 1, 2, and the currents were measured. The results are shown in FIG. 6A. Nanopore sequencer 1 (pore 1) exhibited an asymmetric response when reverse-biased, known as "gating"; and nanopore sequencer 2 (pore 2) exhibited a symmetric response.

Figure 6B:
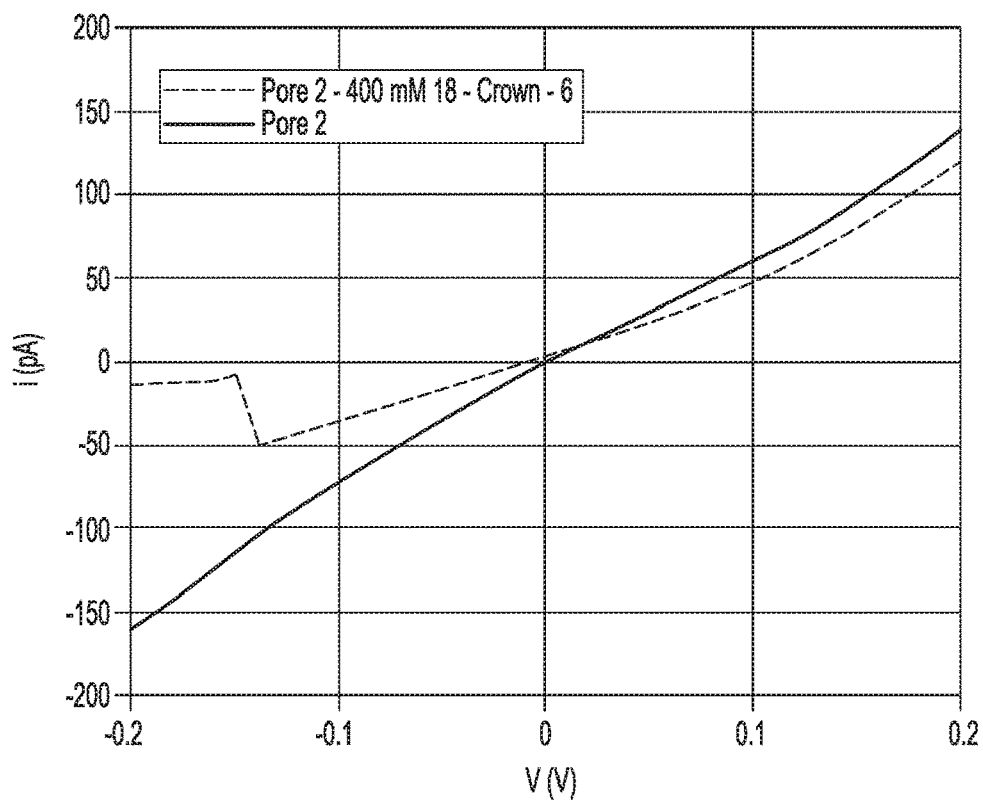

The potassium chloride was perfused from both the cis and trans wells of nanopore sequencer 2. A crown ether, 18-crown-6, was added to potassium chloride at 400 mM, and this electrolyte was introduced into the cis and trans wells of the nanopore sequencer 2. Various voltage potentials were applied across the nanopore in the nanopores sequencer 2, and the current was measured. The results are shown in FIG. 6B. FIG. 6B also shows the results for nanopore sequencer 2 from FIG. 6A (without the crown ether) for comparison. When the crown ether was added, the nanopore sequencer 2 exhibited suppression of the current in both the forward and reverse bias direction. The reduction of conduction at both the negative bias and the positive bias confirmed that the 18-crown-6 impeded the $K^+$ transport through the MspA nanopore. This result suggests that complexation of the $K^+$ ions with the crown ether impedes $K^+$ ion transport through the nanopore by reducing the current that flows by the expected factor of 2×.

Figure 6C:
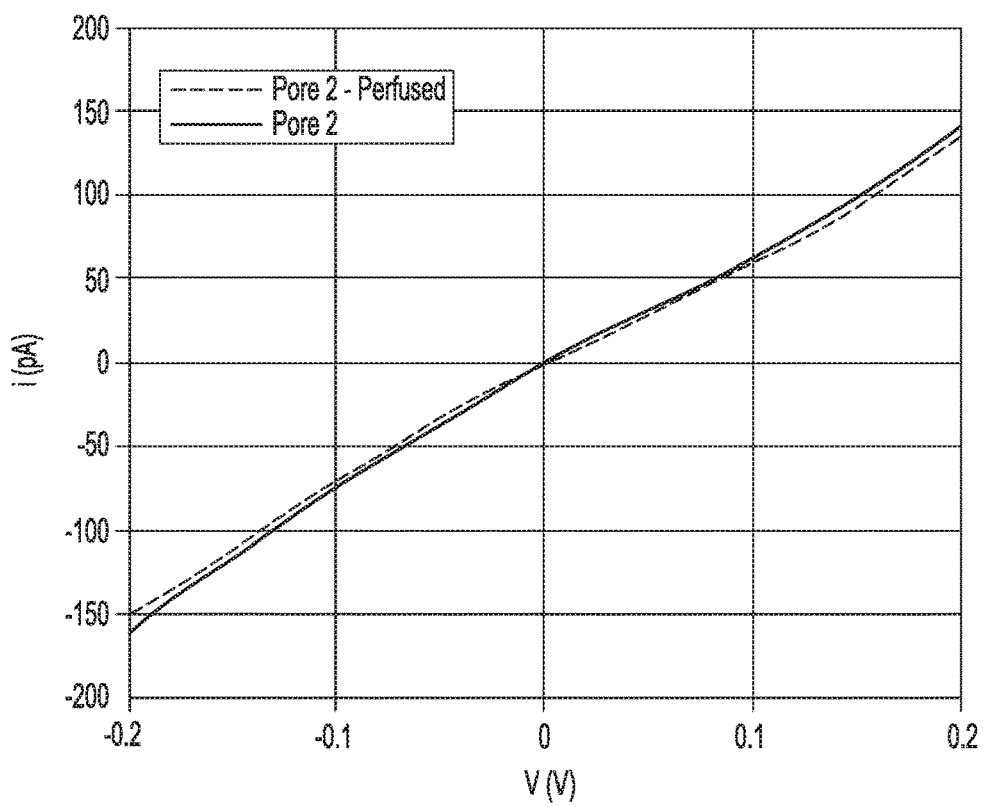

The potassium chloride with the crown ether was then perfused from the cis well of nanopore sequencer 2. As the cis and trans wells were separated by a lipid layer, potassium chloride with added crown ether remained in the trans well of nanopore sequencer 2. Various voltage potentials were applied across the nanopore in the nanopore sequencer 2, and the current was measured. The results are shown in FIG. 6C, at the line labeled "pore 2—perfused". FIG. 6C also shows the results for nanopore sequencer 2 from FIG. 6A (without the crown ether) for comparison. The IV curve of the nanopore sequencer 2 after the crown ether was perfused (line labeled "pore 2—perfused" in FIG. 6C) returned almost to the standard condition (line labeled "pore 2" in FIG. 6C). Some residual effects were observed on the current transport under reverse bias, which was consistent with small amounts of the crown ether remaining trapped in the trans well.

Example 2

An oligomer having a hairpin structure with 87 nucleotide bases and a melting temperature of 66° C. was used in a translocation experiment. Two nanopore sequencers were used. Each had a single cis well and a single trans well, and an MspA nanopore positioned in a lipid bilayer membrane between the cis well and the trans well.

In the comparative sequencer, potassium chloride, without any crown ether added thereto, was introduced into the cis and trans wells. In the example sequencer, potassium chloride with 400 mM 18-crown 6 added thereto, was introduced into the cis and trans wells. Respective oligomers were translocated through the comparative sequencer and the example sequencer.

Figure 7A:
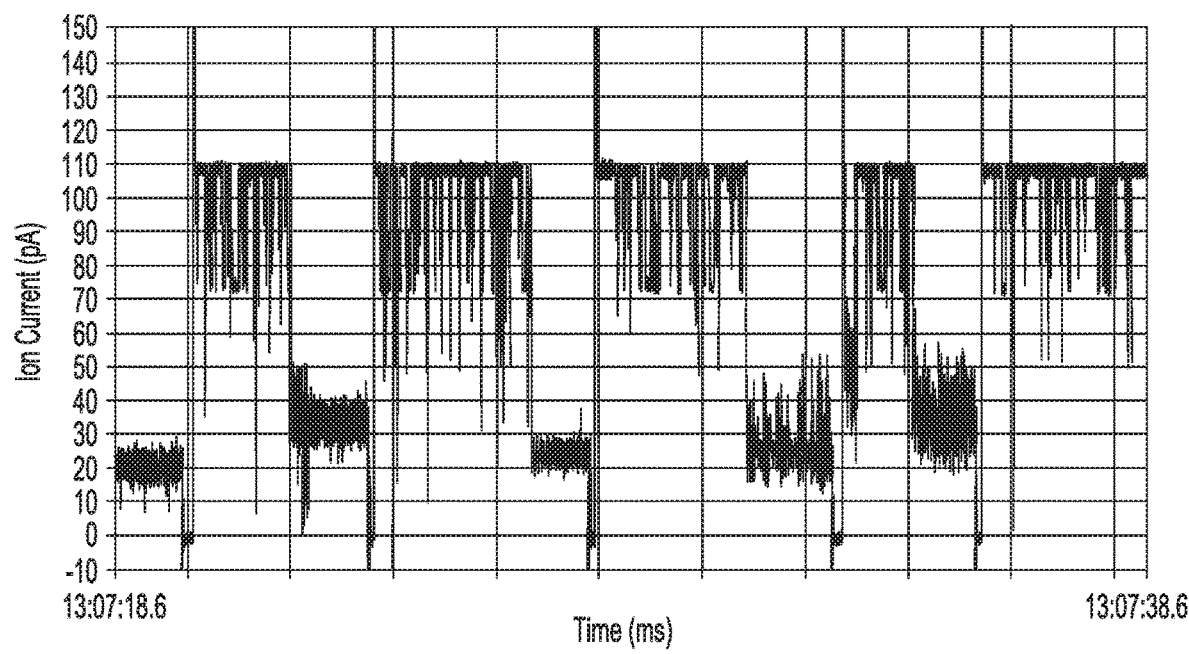
FIG. 7A is a graph illustrating the ion current (pA) versus time (ms) for a hairpin translocation through a single *Mycobacterium smegmatis* porin A (MspA) pore without a crown ether added.
Figure 7B:
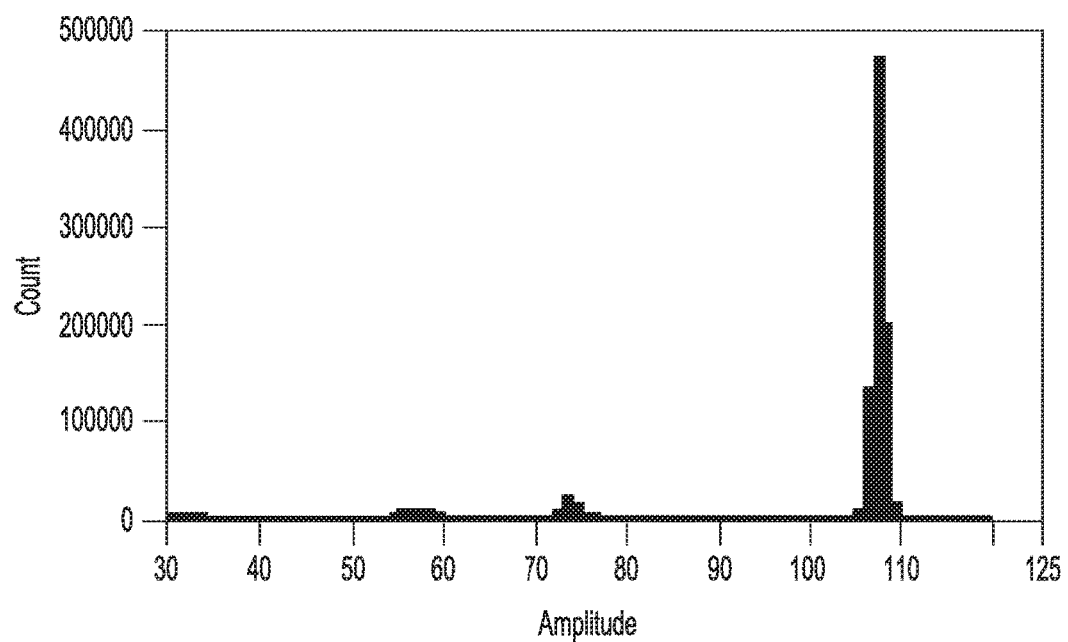
FIG. 7B is a histogram (count versus amplitude) of the data presented in FIG. 7A.

The ion current versus time results for the comparative sequencer are shown in FIG. 7A, and a histogram of the results is shown in FIG. 7B. For the comparative sequencer, the open pore current was 107.5 pA and the middle blockade current was 73.5 pA (68%). The readings between 20 pA and 50 pA in FIG. 7A are believed to correspond to a deep blockade, where the hairpin DNA oligomer unzips and there is a stall in translocation. In the histogram, it is believed that this deep blockade is seen between the amplitude of 70 and 80.

Figure 8A:
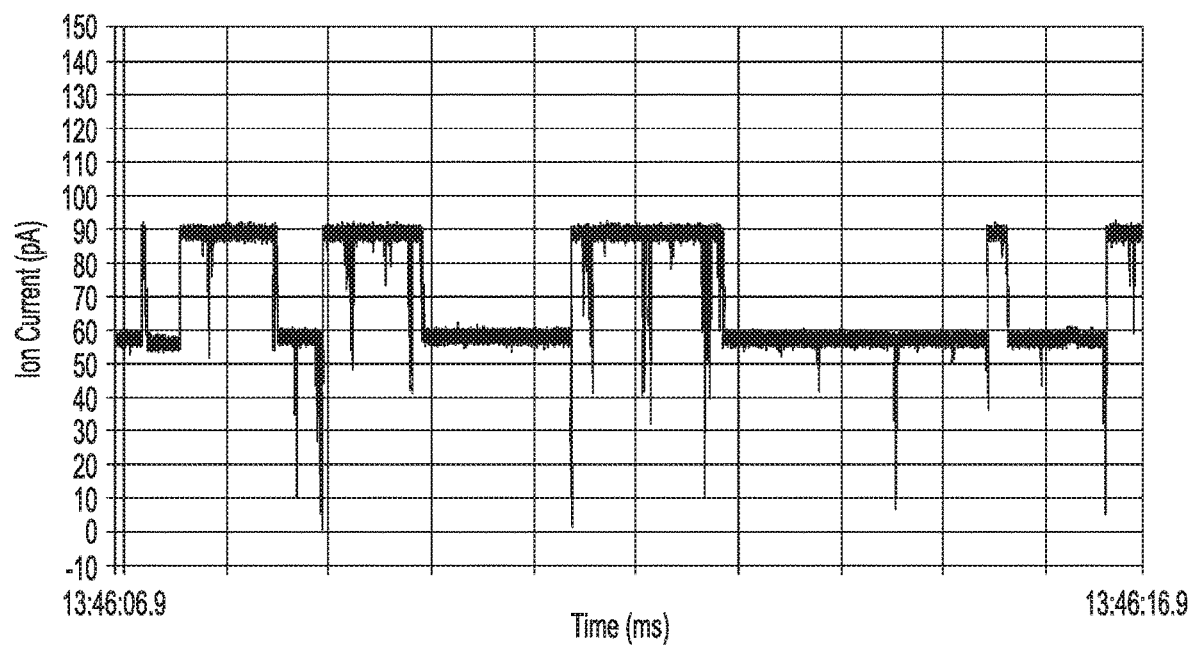
FIG. 8A is a graph illustrating the ion current (pA) versus time (ms) for a hairpin translocation through a single MspA pore with a crown ether added.
Figure 8B:
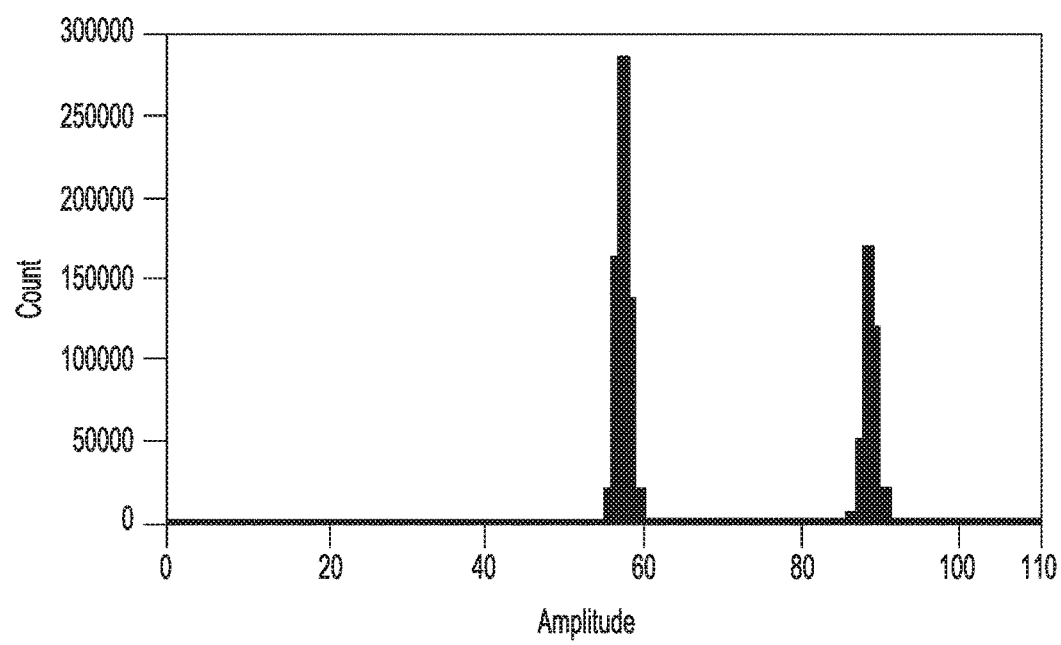
FIG. 8B is a histogram (count versus amplitude) of the data presented in FIG. 8A.

The ion current versus time results for the example sequencer are shown in FIG. 8A, and a histogram of the results is shown in FIG. 8B. For the example sequencer, the open pore current was 88.5 pA and the middle blockade current was 57.5 pA (65%). As depicted in FIG. 8A, there is a reduced number of readings between 20 pA and 50 pA. It is believed that the complexation of the $K^+$ ions renders it easier for the DNA to unzip, thus reducing the deep blockade. In FIG. 8B, it is observed that there is no signal between the amplitude of 70 and 80, also supporting the notion that the deep blockade is reduced or eliminated.

Overall, the current level shifts of the example sequencer are consistent with the reduction of the contribution of the $K^+$ ions to the conduction through the nanopore. It is believed that this, in turn, will reduce $Cl^-$ ion depletion.

Additional Notes

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

Reference throughout the specification to "one example", "another example", "an example", and so forth, means that a particular element (e.g., feature, structure, and/or characteristic) described in connection with the example is included in at least one example described herein, and may or may not be present in other examples. In addition, it is to be understood that the described elements for any example may be combined in any suitable manner in the various examples unless the context clearly dictates otherwise.

It is to be understood that the ranges provided herein include the stated range and any value or sub-range within the stated range. For example, a range from about 50 mM to about 500 mM should be interpreted to include not only the explicitly recited limits of from about 50 mM to about 500 mM, but also to include individual values, such as about 100 mM, about 335 mM, about 400.5 mM, about 490 mM, etc., and sub-ranges, such as from about 75 mM to about 475 mM, from about 200 mM to about 300 mM, etc. Furthermore, when "about" and/or "substantially" are/is utilized to describe a value, this is meant to encompass minor variations (up to +/−10%) from the stated value.

While several examples have been described in detail, it is to be understood that the disclosed examples may be modified. Therefore, the foregoing description is to be considered non-limiting.

What is claimed is:

1. A nanopore sequencer, comprising:
   a cis well;
   a trans well;
   a nanopore fluidically connecting the cis well and the trans well; and
   a modified electrolyte in the cis well, or the trans well, or the cis and trans wells, the modified electrolyte including an electrolyte and a cation complexing agent;
   wherein:
   the modified electrolyte is in the cis well, the nanopore sequencer further comprises a non-modified electrolyte in the trans well, and the non-modified electrolyte includes the electrolyte without the cation complexing agent; or
   the modified electrolyte is in the trans well, the nanopore sequencer further comprises the non-modified electrolyte in the cis well, and the non-modified electrolyte includes the electrolyte without the cation complexing agent.

2. The nanopore sequencer as defined in claim 1, further comprising a plurality of the trans wells defined in a substrate, each of which is fluidically connected to the cis well by a respective nanopore, wherein a density of the plurality of trans wells ranges from about 10 trans wells per $mm^2$ of the substrate to about 1,000,000 trans wells per $mm^2$ of the substrate.

3. The nanopore sequencer as defined in claim 1, wherein the modified electrolyte includes greater than 0 mM to about 500 mM of the cation complexing agent.

4. A nanopore sequencer, comprising:
   a cis well;
   a trans well;
   a nanopore fluidically connecting the cis well and the trans well; and
   a modified electrolyte in the cis well, or the trans well, or the cis and trans wells, the modified electrolyte including an electrolyte and a cation complexing agent;
   wherein:
   the electrolyte includes a potassium cation and an associated anion, a sodium cation and the associated anion, or combinations thereof; and
   the cation complexing agent is selected from the group consisting of a crown ether, a calixarene, valinomycin, and derivatives thereof.

5. The nanopore sequencer as defined in claim 4, further comprising a plurality of the trans wells defined in a substrate, each of which is fluidically connected to the cis well by a respective nanopore, wherein a density of the plurality of trans wells ranges from about 10 trans wells per $mm^2$ of the substrate to about 1,000,000 trans wells per $mm^2$ of the substrate.

6. The nanopore sequencer as defined in claim 4, wherein the modified electrolyte includes greater than 0 mM to about 500 mM of the cation complexing agent.

7. A method of using a nanopore sequencer, the nanopore sequencer comprising:
   a cis well;
   a trans well;
   a nanopore fluidically connecting the cis well and the trans well; and
   a modified electrolyte in the cis well, or the trans well, or the cis and trans wells, the modified electrolyte including an electrolyte and a cation complexing agent;
   wherein the method comprises:
      controlling depletion of a redox reagent of the electrolyte in the nanopore sequencer by applying a voltage bias ranging from about −1 V to about 1 V between the cis well of the nanopore sequencer and the trans well of the nanopore sequencer.

8. The method as defined in claim 7, further comprising providing the nanopore sequencer with:
   the modified electrolyte in the cis well, and the electrolyte, without the cation complexing agent, in the trans well; or
   the modified electrolyte in the trans well, and the electrolyte, without the cation complexing agent, in the cis well.

9. The method as defined in claim 7, further comprising:
   incorporating the cation complexing agent into the electrolyte to form the modified electrolyte; and
   introducing the modified electrolyte to the cis well, or the trans well, or the cis and trans wells.

10. The method as defined in claim 7, wherein:
    the electrolyte includes a potassium cation and an associated anion, a sodium cation and the associated anion, or combinations thereof; and
    the cation complexing agent is selected from the group consisting of a crown ether, a calixarene, valinomycin, and derivatives thereof.

11. A nanopore sequencer, comprising:
    a cis well;
    a trans well;
    a nanopore fluidically connecting the cis well and the trans well; and
    a polyelectrolyte in a gel state in the cis well, or the trans well, or the cis and trans wells.

12. The nanopore sequencer as defined in claim 11, wherein:
    the polyelectrolyte is in the cis well, and the nanopore sequencer further comprises an electrolyte in the trans well; or
    the polyelectrolyte is in the trans well, and the nanopore sequencer further comprises an electrolyte in the cis well.

13. The nanopore sequencer as defined in claim 12, wherein:
    the polyelectrolyte is selected from the group consisting of polydiallyldimethylammonium chloride, an ionic form of polyethyleneimine, an ionic form of linear polyethyleneimine, poly(allylamine hydrochloride), and an ionic form of poly(4-vinylpyridine); and
    the electrolyte includes a potassium cation and an associated anion, a sodium anion and the associated anion, or combinations thereof.

14. The nanopore sequencer as defined in claim 11, further comprising a plurality of the trans wells defined in a substrate, each of which is fluidically connected to the cis well by a respective nanopore, and wherein a density of the plurality of trans wells ranges from about 10 trans wells per $mm^2$ of the substrate to about 1,000,000 trans wells per $mm^2$ of the substrate.

15. The nanopore sequencer as defined in claim 11, wherein:
    the polyelectrolyte is present in both the cis and trans wells; and
    the polyelectrolyte is selected from the group consisting of polydiallyldimethylammonium chloride, an ionic form of polyethyleneimine, an ionic form of linear polyethyleneimine, poly(allylamine hydrochloride), and an ionic form of poly(4-vinylpyridine).

16. A method of using the nanopore sequencer of claim 11, the method comprising:
    controlling depletion of a redox reagent of the polyelectrolyte in the nanopore sequencer by applying a voltage bias ranging from about −1 V to about 1 V between the cis well of the nanopore sequencer and the trans well of the nanopore sequencer.

17. A nanopore sequencer, comprising:
    a cis well;
    a trans well;
    a nanopore fluidically connecting the cis well and the trans well;
    a cis well electrode structure associated with the cis well, the cis well electrode structure including a first base electrode and a redox solid immobilized to the first base electrode;
    a trans well electrode structure associated with the trans well, the trans well electrode structure including a second base electrode and the redox solid immobilized to the second base electrode; and
    an electrolyte including a cation to be consumed or released in response to respective redox reactions at the cis well electrode structure and the trans well electrode structure.

18. The nanopore sequencer as defined in claim 17, wherein the redox solid is selected from the group consisting of tetracyanoquinodimethane (TCNQ), Prussian blue, and polypyrrole.

19. The nanopore sequencer as defined in claim 17, wherein the first and second base electrodes are independently selected from the group consisting of graphite, platinum, gold, silver, copper, carbon fiber, diamond, and palladium.

20. A method of using the nanopore sequencer of claim 17, the method comprising:
    controlling depletion of a redox reagent of the electrolyte in the nanopore sequencer by:
       applying a first voltage to the cis well electrode structure, thereby initiating a cathodic reaction that consumes a cation of the electrolyte in the nanopore sequencer; and
       applying a second voltage to the trans well electrode structure, thereby initiating an anodic reaction that releases the cation of the electrolyte.

21. The method as defined in claim 20, wherein the redox solid is selected from the group consisting of tetracyanoquinodimethane (TCNQ), Prussian blue, and polypyrrole.

* * * * *